US009364328B2

(12) United States Patent
Southard et al.

(10) Patent No.: US 9,364,328 B2
(45) Date of Patent: Jun. 14, 2016

(54) MULTI-PIECE MACHINE GRAFT SYSTEMS AND METHODS

(71) Applicant: AlloSource, Centennial, CO (US)

(72) Inventors: Matthew Southard, Englewood, CO (US); Matthew Peterson, Thornton, CO (US); Nate Henriod, Holladay, UT (US); Robert L. Bundy, The Woodlands, TX (US)

(73) Assignee: AlloSource, Centennial, CO (US)

( * ) Notice: Subject to any disclaimer, the term of this patent is extended or adjusted under 35 U.S.C. 154(b) by 0 days.

(21) Appl. No.: 14/584,292

(22) Filed: Dec. 29, 2014

(65) Prior Publication Data

US 2015/0173902 A1    Jun. 25, 2015

Related U.S. Application Data

(63) Continuation of application No. 13/680,222, filed on Nov. 19, 2012, now Pat. No. 8,920,511.

(60) Provisional application No. 61/561,002, filed on Nov. 17, 2011, provisional application No. 61/684,218, filed on Aug. 17, 2012.

(51) Int. Cl.
*A61F 2/28* (2006.01)
*A61F 2/44* (2006.01)
(Continued)

(52) U.S. Cl.
CPC ............... *A61F 2/28* (2013.01); *A61F 2/30744* (2013.01); *A61F 2/30942* (2013.01); *A61F 2/44* (2013.01); *A61F 2/4455* (2013.01); *A61F 2/4465* (2013.01); *A61F 2/4644* (2013.01); *A61F 2/30965* (2013.01); *A61F 2/442* (2013.01); *A61F 2/447* (2013.01); *A61F 2/4611* (2013.01); *A61F 2002/2817* (2013.01); *A61F 2002/2835* (2013.01); *A61F 2002/2839* (2013.01); *A61F 2002/305* (2013.01); *A61F 2002/3038* (2013.01); *A61F 2002/3055* (2013.01);
(Continued)

(58) Field of Classification Search
CPC ................ A61F 2/4455; A61F 2/4644; A61F 2002/2835; A61F 2002/2839; A61F 2002/30733
See application file for complete search history.

(56) References Cited

U.S. PATENT DOCUMENTS

| 4,627,853 | A | 12/1986 | Campbell et al. |
| 5,073,373 | A | 12/1991 | O'Leary et al. |

(Continued)

FOREIGN PATENT DOCUMENTS

| WO | 2012135205 | 10/2012 |
| WO | 2013047936 | 4/2013 |

OTHER PUBLICATIONS

International Search Report and Written Opinion mailed on Apr. 9, 2013 for International Patent Application No. PCT/US2012/65832 filed Nov. 19, 2012, all pages.
(Continued)

*Primary Examiner* — Brian Dukert
(74) *Attorney, Agent, or Firm* — Kilpatrick Townsend & Stockton LLP

(57) ABSTRACT

Embodiments of the present invention encompass graft assemblies, and methods for their use and manufacture. An exemplary bone graft assembly includes first and second bone pieces having respective mating features which, when combined, define non-uniform press fit. Related embodiments encompass graft assemblies having enclosed or hidden mating features.

24 Claims, 31 Drawing Sheets

(51) Int. Cl.
*A61F 2/30* (2006.01)
*A61F 2/46* (2006.01)
(52) U.S. Cl.
CPC ............. *A61F 2002/30057* (2013.01); *A61F 2002/30062* (2013.01); *A61F 2002/3079* (2013.01); *A61F 2002/3082* (2013.01); *A61F 2002/30112* (2013.01); *A61F 2002/30115* (2013.01); *A61F 2002/30126* (2013.01); *A61F 2002/30131* (2013.01); *A61F 2002/30133* (2013.01); *A61F 2002/30138* (2013.01); *A61F 2002/30148* (2013.01); *A61F 2002/30151* (2013.01); *A61F 2002/30153* (2013.01); *A61F 2002/30154* (2013.01); *A61F 2002/30158* (2013.01); *A61F 2002/30166* (2013.01); *A61F 2002/30228* (2013.01); *A61F 2002/30233* (2013.01); *A61F 2002/30322* (2013.01); *A61F 2002/30324* (2013.01); *A61F 2002/30327* (2013.01); *A61F 2002/30329* (2013.01); *A61F 2002/30332* (2013.01); *A61F 2002/30354* (2013.01); *A61F 2002/30377* (2013.01); *A61F 2002/30382* (2013.01); *A61F 2002/30383* (2013.01); *A61F 2002/30387* (2013.01); *A61F 2002/30448* (2013.01); *A61F 2002/30477* (2013.01); *A61F 2002/30487* (2013.01); *A61F 2002/30593* (2013.01); *A61F 2002/30599* (2013.01); *A61F 2002/30604* (2013.01); *A61F 2002/30616* (2013.01); *A61F 2002/30617* (2013.01); *A61F 2002/30733* (2013.01); *A61F 2002/30772* (2013.01); *A61F 2002/30782* (2013.01); *A61F 2002/30785* (2013.01); *A61F 2002/30787* (2013.01); *A61F 2002/30841* (2013.01); *A61F 2002/30892* (2013.01); *A61F 2002/30894* (2013.01); *A61F 2002/30897* (2013.01); *A61F 2002/30952* (2013.01); *A61F 2002/30971* (2013.01); *A61F 2002/30975* (2013.01); *A61F 2002/4475* (2013.01); *A61F 2250/006* (2013.01); *A61F 2310/00017* (2013.01); *A61F 2310/00023* (2013.01); *A61F 2310/00359* (2013.01); *Y10T 29/49826* (2015.01)

(56) References Cited

U.S. PATENT DOCUMENTS

| | | |
|---|---|---|
| 5,284,655 A | 2/1994 | Bogdansky et al. |
| 5,314,476 A | 5/1994 | Prewett et al. |
| 5,405,390 A | 4/1995 | O'Leary et al. |
| 5,439,684 A | 8/1995 | Prewett et al. |
| 5,507,813 A | 4/1996 | Dowd et al. |
| 5,510,396 A | 4/1996 | Prewett et al. |
| 5,531,791 A | 7/1996 | Wolfinbarger |
| 5,556,379 A | 9/1996 | Wolfinbarger |
| 5,676,146 A | 10/1997 | Scarborough |
| 5,707,962 A | 1/1998 | Chen et al. |
| 5,749,874 A | 5/1998 | Schwartz |
| 5,769,899 A | 6/1998 | Schwartz et al. |
| 5,788,941 A | 8/1998 | Dalmasso et al. |
| 5,797,871 A | 8/1998 | Wolfinbarger |
| 5,820,581 A | 10/1998 | Wolfinbarger |
| 5,861,041 A | 1/1999 | Tienboon |
| 5,895,426 A | 4/1999 | Scarborough et al. |
| 5,948,428 A | 9/1999 | Lee et al. |
| 5,972,368 A | 10/1999 | McKay |
| 5,976,104 A | 11/1999 | Wolfinbarger |
| 5,977,034 A | 11/1999 | Wolfinbarger |
| 5,977,432 A | 11/1999 | Wolfinbarger |
| 6,024,735 A | 2/2000 | Wolfinbarger |
| 6,090,998 A | 7/2000 | Grooms et al. |
| 6,180,606 B1 | 1/2001 | Chen et al. |
| 6,189,537 B1 | 2/2001 | Wolfinbarger |
| 6,200,347 B1 | 3/2001 | Anderson et al. |
| 6,214,369 B1 | 4/2001 | Grande |
| 6,290,724 B1 | 9/2001 | Marino |
| 6,294,041 B1 | 9/2001 | Boyce et al. |
| 6,294,187 B1 | 9/2001 | Boyce et al. |
| 6,305,379 B1 | 10/2001 | Wolfinbarger |
| 6,315,795 B1 | 11/2001 | Scarborough et al. |
| 6,340,477 B1 | 1/2002 | Anderson |
| 6,371,988 B1 | 4/2002 | Pafford et al. |
| 6,436,138 B1 | 8/2002 | Dowd |
| 6,464,983 B1 | 10/2002 | Grotendorst |
| 6,478,825 B1 | 11/2002 | Winterbottom et al. |
| 6,482,231 B1 | 11/2002 | Abatangelo |
| 6,482,233 B1 | 11/2002 | Aebi et al. |
| 6,511,509 B1 | 1/2003 | Ford et al. |
| 6,576,015 B2 | 6/2003 | Geistlich et al. |
| 6,616,698 B2 | 9/2003 | Scarborough |
| 6,632,247 B2 | 10/2003 | Boyer, II et al. |
| 6,652,593 B2 | 11/2003 | Boyer, II et al. |
| 6,685,626 B2 | 2/2004 | Wironen |
| 6,696,073 B2 | 2/2004 | Boyce et al. |
| 6,716,245 B2 | 4/2004 | Pasquet et al. |
| 6,746,484 B1 | 6/2004 | Liu et al. |
| 6,800,480 B1 | 10/2004 | Bodnar et al. |
| 6,805,713 B1 | 10/2004 | Carter et al. |
| 6,808,585 B2 | 10/2004 | Boyce et al. |
| 6,837,907 B2 | 1/2005 | Wolfinbarger |
| 6,855,167 B2 | 2/2005 | Shimp et al. |
| 6,855,169 B2 | 2/2005 | Boyer et al. |
| 6,863,694 B1 | 3/2005 | Boyce et al. |
| 6,902,578 B1 | 6/2005 | Anderson et al. |
| 6,911,045 B2 | 6/2005 | Shimp |
| 6,911,212 B2 | 6/2005 | Gertzman et al. |
| 7,018,412 B2 | 3/2006 | Ferreira et al. |
| 7,048,765 B1 | 5/2006 | Grooms et al. |
| 7,115,146 B2 | 10/2006 | Boyer et al. |
| 7,132,110 B2 | 11/2006 | Kay et al. |
| 7,163,691 B2 | 1/2007 | Knaack et al. |
| 7,172,629 B2 | 2/2007 | McKay |
| 7,182,781 B1 | 2/2007 | Bianchi et al. |
| 7,241,874 B2 | 7/2007 | Thorne |
| 7,252,685 B2 | 8/2007 | Bindseil et al. |
| 7,297,540 B2 | 11/2007 | Mitrani |
| 7,316,822 B2 | 1/2008 | Binette et al. |
| 7,323,011 B2 | 1/2008 | Shepard et al. |
| 7,335,381 B2 | 2/2008 | Malinin |
| 7,351,262 B2 | 4/2008 | Bindseil et al. |
| 7,371,409 B2 | 5/2008 | Petersen et al. |
| 7,491,237 B2 | 2/2009 | Randall et al. |
| 7,498,040 B2 | 3/2009 | Masinaei et al. |
| 7,582,309 B2 | 9/2009 | Rosenberg et al. |
| 7,608,113 B2 | 10/2009 | Boyer et al. |
| 7,622,562 B2 | 11/2009 | Thorne et al. |
| 7,662,185 B2 | 2/2010 | Alfaro et al. |
| 7,726,002 B2 | 6/2010 | Shimp et al. |
| 7,753,963 B2 | 7/2010 | Boyer, II et al. |
| 7,785,634 B2 | 8/2010 | Borden |
| 7,807,458 B2 | 10/2010 | Schiller |
| 7,811,608 B2 | 10/2010 | Kay et al. |
| 7,815,926 B2 | 10/2010 | Syring et al. |
| 7,837,740 B2 | 11/2010 | Semler et al. |
| 7,875,296 B2 | 1/2011 | Binette et al. |
| 7,879,103 B2 | 2/2011 | Gertzman et al. |
| 7,883,511 B2 | 2/2011 | Fernyhough |
| 7,931,692 B2 | 4/2011 | Sybert et al. |
| 8,002,813 B2 | 8/2011 | Scarborough et al. |
| 8,002,837 B2 | 8/2011 | Stream et al. |
| 8,012,211 B2 | 9/2011 | Kuslich |
| 8,021,692 B2 | 9/2011 | Hiles |
| 8,025,896 B2 | 9/2011 | Malaviya et al. |
| 8,039,016 B2 | 10/2011 | Drapeau et al. |
| 8,133,421 B2 | 3/2012 | Boyce et al. |
| 8,137,702 B2 | 3/2012 | Binette et al. |
| 8,163,549 B2 | 4/2012 | Yao et al. |
| 8,167,943 B2 | 5/2012 | Carter et al. |
| 8,197,474 B2 | 6/2012 | Scarborough et al. |
| 8,202,539 B2 | 6/2012 | Behnam et al. |

(56) References Cited

U.S. PATENT DOCUMENTS

| | | |
|---|---|---|
| 8,268,008 B2 | 9/2012 | Betz et al. |
| 8,292,968 B2 | 10/2012 | Truncale et al. |
| 8,328,876 B2 | 12/2012 | Behnam et al. |
| 8,343,229 B2 | 1/2013 | Coale |
| 8,389,017 B1 | 3/2013 | Starling et al. |
| 8,399,010 B2 | 3/2013 | McKay |
| 8,403,991 B2 | 3/2013 | Ullrich, Jr. et al. |
| 8,409,623 B2 | 4/2013 | Shim et al. |
| 8,435,566 B2 | 5/2013 | Behnam et al. |
| 8,496,970 B2 | 7/2013 | Binette et al. |
| 8,506,632 B2 | 8/2013 | Ganem et al. |
| 8,551,176 B2 | 10/2013 | Ullrich, Jr. et al. |
| 8,563,040 B2 | 10/2013 | Marchosky |
| 8,574,825 B2 | 11/2013 | Shelby et al. |
| 8,585,766 B2 | 11/2013 | Ullrich, Jr. et al. |
| 8,722,075 B2 | 5/2014 | Shimp et al. |
| 8,771,368 B2 | 7/2014 | McKay |
| 8,859,007 B2 | 10/2014 | Carter et al. |
| 8,920,511 B2 | 12/2014 | Southard et al. |
| 8,992,964 B2 | 3/2015 | Shelby et al. |
| 9,029,077 B2 | 5/2015 | Song et al. |
| 9,162,012 B2 | 10/2015 | Benham et al. |
| 2002/0138143 A1 | 9/2002 | Grooms et al. |
| 2003/0181980 A1* | 9/2003 | Berry .................... A61F 2/4455 623/17.11 |
| 2006/0241763 A1* | 10/2006 | Paul ........................ A61F 2/28 623/17.11 |
| 2006/0276907 A1 | 12/2006 | Boyer et al. |
| 2007/0185231 A1 | 8/2007 | Liu et al. |
| 2008/0058953 A1 | 3/2008 | Scarborough |
| 2008/0249632 A1 | 10/2008 | Stone et al. |
| 2008/0249638 A1 | 10/2008 | Asgari |
| 2008/0305145 A1 | 12/2008 | Shelby et al. |
| 2010/0168869 A1 | 7/2010 | Long et al. |
| 2010/0196333 A1 | 8/2010 | Gaskins et al. |
| 2010/0241228 A1 | 9/2010 | Syring et al. |
| 2011/0070271 A1 | 3/2011 | Truncale et al. |
| 2011/0125003 A1 | 5/2011 | Reach |
| 2012/0082704 A1 | 4/2012 | Phillips et al. |
| 2012/0213859 A1 | 8/2012 | Shelby et al. |
| 2012/0251609 A1 | 10/2012 | Huang et al. |
| 2013/0189338 A1 | 7/2013 | Drapeau et al. |
| 2014/0093543 A1 | 4/2014 | Morreale |
| 2014/0121772 A1 | 5/2014 | Emerton et al. |
| 2014/0170232 A1 | 6/2014 | Shelby et al. |
| 2014/0205674 A1 | 7/2014 | Wei |
| 2014/0208980 A1 | 7/2014 | Song et al. |
| 2014/0212471 A1 | 7/2014 | Drapeau et al. |
| 2014/0212499 A1 | 7/2014 | Cooper et al. |
| 2014/0220142 A1 | 8/2014 | Song et al. |
| 2014/0255506 A1 | 9/2014 | Behnam et al. |
| 2014/0314822 A1 | 10/2014 | Carter et al. |
| 2014/0342013 A1 | 11/2014 | He et al. |
| 2015/0004247 A1 | 1/2015 | Carter et al. |
| 2015/0012107 A1 | 1/2015 | Koford et al. |
| 2015/0093429 A1 | 4/2015 | Carter et al. |
| 2015/0174295 A1 | 6/2015 | Woodell-May et al. |
| 2015/0182667 A1 | 7/2015 | Guelcher et al. |
| 2015/0202345 A1 | 7/2015 | Shelby et al. |
| 2015/0202346 A1 | 7/2015 | Shelby et al. |
| 2015/0251361 A1 | 9/2015 | Meyer et al. |
| 2015/0258244 A1 | 9/2015 | Shelby et al. |
| 2015/0306278 A1 | 10/2015 | McKay |

OTHER PUBLICATIONS

International Preliminary Report on Patentability mailed May 30, 2014 for International Patent Application No. PCT/US2012/65832 filed Nov. 19, 2012, all pages.

\* cited by examiner

| MPMG PULL TESTING - 1/20/10 | | |
|---|---|---|
| UNITS - NEWTONS (n) | | |
| CONFIGURATION | POCKET | HEX PIN |
| SAMPLE 1 | 32.25 | 24.60 |
| SAMPLE 2 | 15.70 | 20.40 |
| SAMPLE 3 | 25.60 | 27.10 |
| AVERAGE | 24.52 | 24.30 |

MULTI-PIECE MACHINE GRAFT SYSTEMS AND METHODS

CROSS REFERENCE TO RELATED APPLICATION

This application is a continuation of U.S. Nonprovisional patent application Ser. No. 13/680,222, filed on Nov. 19, 2012, which is a nonprovisional of, and claims the benefit of U.S. Provisional Patent Application No. 61/561,002, filed Nov. 17, 2011, and U.S. Provisional Patent Application No. 61/684,218, filed Aug. 17, 2012, the entire disclosures of which are incorporated herein by reference for all purposes.

BACKGROUND OF THE INVENTION

Embodiments of the present invention are directed in general to the field of medical grafts, and in particular to multi-piece graft compositions, and methods of their use and manufacture.

Medical grafting procedures often involve the implantation of autogenous, allograft, or synthetic grafts into a patient to treat a particular condition or disease. The use of musculoskeletal allograft tissue in reconstructive orthopedic procedures and other medical procedures has markedly increased in recent years, and millions of musculoskeletal allografts have been safely transplanted. A common allograft is bone. Typically, bone grafts are reabsorbed and replaced with the patient's natural bone upon healing. Bone grafts can be used in a variety of indications, including neurosurgical and orthopedic spine procedures for example. In some instances, bone grafts can be used to fuse joints or to repair broken bones.

Allograft and autogenous bone are both derived from humans; the difference is that allograft is harvested from an individual (e.g. donor) other than the one (e.g. patient) receiving the graft. Allograft bone is often taken from cadavers that have donated their bone so that it can be used for living people who are in need of it, for example, patients whose bones have degenerated from cancer. Such tissues represent a gift from the donor or the donor family to enhance the quality of life for other people.

Hence, bone graft compositions and methods are presently available and provide real benefits to patients in need thereof. Yet many advances may still be made to provide improved bone graft systems and methods for treating patients. The bone graft systems and treatment and manufacture methods described herein provide further solutions and answers to these outstanding needs.

BRIEF SUMMARY OF THE INVENTION

Embodiments of the present invention encompass multi-piece graft compositions, and methods for their use and manufacture. For example, bone grafts can be constructed of multiple bone pieces, and can be used in a variety of clinical applications, including without limitation, orthopedic, joint restoration, podiatry, trauma, spine, oral maxillofacial, periodontal, and oncology procedures. Exemplary bone graft configurations include spinal grafts such as textured lordotic cervical spacers, parallel cervical spacers, cortical cervical spacers, cortical/cancellous cervical spacers, transforaminal lumbar interbody fusion (TLIF) spacers, anterior lumbar interbody fusion (ALIF) spacers, posterior lumbar interbody fusion (PLIF) spacers, laminoplasty implants or devices, interspinous implants or devices, femoral rings, fibula rings, radius rings, ulna rings, and any of a variety of wedges, strips, dowels, struts, and the like.

In some instances, embodiments provide techniques for utilizing donated bone or other tissue which is obtained in a variety of sizes, structures, and consistencies. Embodiments also provide effective approaches for producing larger grafts from smaller donor pieces. Hence, use of the processes and products disclosed herein can help to avoid the unwanted waste of donor tissue, while at the same time providing quality, safe, bio-mechanically sound grafts which enable surgeons and patients to achieve positive outcomes. Accordingly, these techniques and systems may increase product availability for allograft spinal orthopedic fusion material by providing structural machined bone allografts, as well as other types of machined grafts. Such grafts are particularly useful in spinal fusion surgeries, and can provide structural support as well as substrate for bone-bone fusion in the intervertebral disc space.

Embodiments of the present invention also provide the ability to join multiple graft pieces, including machine grafts, assembled allografts, and the like, which may be constructed of or include material such as cortical bone, cancellous bone, osteoconductive material, or combinations thereof. In some cases, multi-piece grafts or combined allografts can be manufactured by combining or joining two or more male/female mating features. Graft pieces can be joined, mated, or merged together, optionally without adhesives (e.g. glue) and/or force driven mechanisms (i.e. clamps, vises, screws, pins). This can be accomplished by combining unique geometries with a light press or interference fit to create a different (e.g. larger) machine graft within a particular graft's existing monolithic configuration, function, shape, or quality.

The techniques described herein can be used with any of a variety of graft tissues, including without limitation bone, tendon, and the like. In some cases, multi-piece graft assemblies may include a combination of different types of tissue. For example, a graft or implant assembly may include a bone-tendon-bone (BTB) configuration. In some cases, grafts or implants may also incorporate or include other types of biological materials, such as stem cells.

The present joining or uniting techniques can be used to construct graft design which may otherwise be difficult to achieve due to size constraints typically associated with single pieces of natural donor bone or tissue. For example, the thickness of the cortical wall in human bone, generally the long bones of the legs or arms, rarely exceeds a certain threshold, which can limit the size of grafts that can be produced as a single unit. Further, a large fraction of donors are not suitable to make these kinds of grafts in usable quantities because their bone thickness. Embodiments of the present invention allow a much greater percentage of donor bone to be used for creating grafts or implants.

According to some embodiments, grafts can be implanted within the patient's body using specialized inserter materials, which may include mating features designed to cooperate with corresponding mating features on the graft itself. In certain surgical procedures, the intervertebral space can be manipulated, for example via distraction, and the graft inserted therein. In some cases, a combination of plates and bone screws can be affixed to adjacent vertebrae, and can at least partially cover the operative space.

In one aspect, embodiments of the present invention encompass bone graft assemblies, and systems and methods for their use and manufacture. An exemplary bone graft assembly includes a first bone piece having a first mating feature, and a second bone piece having a second mating feature. The first mating feature has a shape that is non-complimentary to a shape of the second mating feature, such that when the first and second bone pieces are coupled, an interface between the first and second mating features is defined by a non-uniform press fit. In some cases, the first mating feature has a polygon shape, and the second mating feature has e a curved shape. In some cases, the polygon shape is a regular polygon shape, an irregular polygon shape, an equilateral polygon shape, or a cyclic polygon shape. In some cases, the first mating feature has an irregular hexagon shape, and the second mating feature has a racetrack shape. In some cases, curved shape can be an oval shape, an ovoid shape, an elliptical shape, a slot shape, or a canal shape. In some cases, the first mating feature has an inscribed polygon shape, and the second mating feature has an inscribed racetrack shape. In some cases, the first mating feature shape includes a corner segment, and the second mating feature shape includes an arc segment, such that when the first and second bone pieces are coupled, the corner and arc segments are pressed together. In some instances, corner and arc segments both deform non-uniformly when the first and second bone pieces are coupled.

In another aspect, embodiments of the present invention encompass bone graft assemblies having a first bone piece with a first mating feature, and a second bone piece with a second mating feature, and the first and second mating features are configured to provide, when approximated, a hidden engagement zone. In some cases, the first mating feature includes a peripheral surface, a medial surface, an inner surface, and a core surface, and the second mating feature includes an outer surface, a peripheral surface, a medial engagement surface, and an inner surface. In some cases, the first and second mating features are configured to provide, when approximated, a peripheral engagement zone defined between at least portions of the peripheral surfaces of the first and second mating features, respectively, a medial engagement zone defined between at least portions of the medial surfaces of the first and second mating features, respectively, and an inner engagement zone defined between at least portions of the inner surfaces of the first and second mating features, respectively. In some cases, the inner engagement zone is disposed interior to the medial engagement zone. In some cases, the medial engagement zone is disposed interior to the peripheral engagement zone, and wherein at least a portion of the medial engagement zone is disposed between the core surface of the first mating feature and the outer surface of the second mating feature. According to some embodiments, the first and second mating features are configured to provide, when approximated, a continuous aperture that extends through the first and second bone pieces of the assembly. In some instances, the continuous aperture is at least partially defined by the first and second mating features. In some instances, the continuous aperture is not at least partially defined by the first and second mating features. In some instances, the first mating feature includes an annular wall disposed between the first mating feature medial and core surfaces, and the second mating feature includes a second annular wall disposed between the second mating feature medial and outer surfaces. Optionally, the second annular wall can be configured to slidingly receive the first annular wall. In some instances, the first and second mating features are configured to provide, when approximated, a press fit at the medial engagement zone. According to certain embodiments, a first mating feature medial surface is disposed interior to and angularly offset from the first mating feature peripheral surface, a first mating feature inner surface is disposed interior to and angularly offset from the first mating feature medial surface, and a first mating feature core surface is disposed interior to and angularly offset from the first mating feature inner surface. According to certain embodiments, a second mating feature peripheral surface is disposed interior to and angularly offset from the second mating feature outer surface, a second mating feature medial surface is disposed interior to and angularly offset from the second mating feature peripheral surface, and a second mating feature inner surface is disposed interior to and angularly offset from the second mating feature medial surface.

In yet another aspect, embodiments of the present invention encompass methods of manufacturing or constructing a bone graft assembly which include obtaining a first bone piece, processing the first bone piece to produce a first mating feature thereon, obtaining a second bone piece, and processing the second bone piece to produce a second mating feature thereon. In certain embodiments, the first mating feature has a shape that is non-complimentary to a shape of the second mating feature, such that when the first and second bone pieces are coupled, an interface between the first and second mating features is defined by a non-uniform press fit. In some instances, the processing of the first bone piece is performed at least in part using a computer numerical control (CNC) apparatus.

In still another aspect, embodiments of the present invention encompass methods of manufacturing or constructing a bone graft assembly which include obtaining a first bone piece, processing the first bone piece to produce a first mating feature thereon, obtaining a second bone piece, and processing the second bone piece to produce a second mating feature thereon. In certain embodiments, the first and second mating features are configured to provide, when approximated, a hidden engagement zone. According to some embodiments, the first mating feature includes a peripheral surface, a medial surface, an inner surface, and a core surface. According to some embodiments, the second mating feature includes an outer surface, a peripheral surface, a medial engagement surface, and an inner surface. According to some embodiments, the first and second mating features are configured to provide, when approximated, a peripheral engagement zone defined between at least portions of the peripheral surfaces of the first and second mating features, respectively, a medial engagement zone defined between at least portions of the medial surfaces of the first and second mating features, respectively, an inner engagement zone defined between at least portions of the inner surfaces of the first and second mating features, respectively, and a continuous aperture that extends through the first and second bone pieces of the assembly. According to some embodiments, the inner engagement zone is disposed interior to the medial engagement zone. According to some embodiments, the medial engagement zone is disposed interior to the peripheral engagement zone, and at least a portion of the medial engagement zone is disposed between the core surface of the first mating feature and the outer surface of the second mating feature. In some instances, the processing of the first bone piece is performed at least in part using a computer numerical control (CNC) apparatus.

In still another aspect, embodiments of the present invention encompass methods of treating a patient with a bone graft assembly. For example, a treatment method may include obtaining a bone graft assembly, and administering the bone graft assembly to the patient. In some cases, the bone graft assembly includes a first bone piece having a first mating feature and a second bone piece having a second mating feature. In certain embodiments, the first mating feature has a shape that is non-complimentary to a shape of the second mating feature, such that when the first and second bone pieces are coupled, an interface between the first and second mating features is defined by a non-uniform press fit. In some cases, the bone graft assembly is positioned within the patient's body using an introducer mechanism. In some cases, a portion of the bone graft assembly may include a material such as titanium, polyetherether ketone (PEEK), a steel-based alloy, metal, and stainless steel. In some instances, a first bone piece and a second bone pieced are bonded together with an adhesive. Optionally, the adhesive may include a bone glue. In some instances, the bone graft assembly is administered to a surgical site within or on the patient's body. In some instances, the bone graft assembly is administered to a site adjacent to a bone within the patient. In some instances, the bone graft assembly is administered to a site disposed between opposing bones within the patient. In some instances, the bone graft assembly is administered to a site disposed between opposing vertebrae within the patient. In certain embodiments, the bone graft assembly includes an osteoconductive material and/or an osteoinductive material. In some embodiments, the bone graft assembly includes a stem cell composition. In some instances, the stem cell composition is at least partially disposed within an aperture of the bone graft assembly.

In still yet another aspect, embodiments of the present invention encompass methods of treating a patient with a bone graft assembly, which may include for example, obtaining a bone graft assembly, and administering the bone graft assembly to the patient. In some instances, the bone graft assembly includes a first bone piece having a first mating feature, and a second bone piece having a second mating feature, and the first and second mating features are configured to provide, when approximated, a hidden engagement zone. According to some embodiments, the first mating feature includes a peripheral surface, a medial surface, an inner surface, and a core surface, and the second mating feature includes an outer surface, a peripheral surface, a medial engagement surface, and an inner surface. In certain embodiments, the first and second mating features are configured to provide, when approximated, a peripheral engagement zone defined between at least portions of the peripheral surfaces of the first and second mating features, respectively, a medial engagement zone defined between at least portions of the medial surfaces of the first and second mating features, respectively, an inner engagement zone defined between at least portions of the inner surfaces of the first and second mating features, respectively, and a continuous aperture that extends through the first and second bone pieces of the assembly. According to certain embodiments, the inner engagement zone is disposed interior to the medial engagement zone. According to certain embodiments, the medial engagement zone is disposed interior to the peripheral engagement zone, and at least a portion of the medial engagement zone is disposed between the core surface of the first mating feature and the outer surface of the second mating feature. In some methods, the bone graft assembly is administered to a surgical site within or on the patient's body. In some methods, the bone graft assembly is administered to a site adjacent to a bone within the patient. In some methods, the bone graft assembly is administered to a site disposed between opposing bones within the patient. In some methods, the bone graft assembly is administered to a site disposed between opposing vertebrae within the patient.

In another aspect, embodiments of the present invention encompass bone graft assemblies which include a first bone piece, an intermediate bone piece construct having one or more bone pieces, and a second bone piece. In exemplary embodiments, a mating feature of the first bone piece has a shape that is non-complimentary to a shape of a first mating feature of the intermediate bone piece construct, and a mating feature of the second bone piece has a shape that is non-complimentary to a shape of a second mating feature of the intermediate bone piece construct. In some instances, the intermediate bone piece construct includes a stack of at least two bone pieces. In some instances, the intermediate bone piece construct includes a bone piece pair having a first bone piece with a first mating feature and a second bone piece with a second mating feature, and the first mating feature of the first bone piece of the bone piece pair has a shape that is non-complimentary to a shape of the second mating feature of the second bone piece of the bone piece pair, such that when the first and second bone pieces of the bone piece pair are coupled, an interface between the first and second mating features of the first and second bone pieces of the bone piece pair is defined by a non-uniform press fit.

In still another aspect, embodiments of the present invention encompass bone graft assemblies which include a first bone piece, an intermediate bone piece construct having one or more bone pieces, and a second bone piece. In certain embodiments, a mating feature of the first bone piece and a first mating feature of the intermediate bone piece construct are configured to provide, when approximated, a first hidden engagement zone, and a mating feature of the second bone piece and a second mating feature of the intermediate bone piece construct are configured to provide, when approximated, a second hidden engagement zone. In some instances, the intermediate bone piece construct includes a stack of at least two bone pieces. In some instances, the intermediate bone piece construct includes a bone piece pair having a first bone piece with a first mating feature and a second bone piece with a second mating feature, and the first mating feature of first bone piece of the bone piece pair and the second mating feature of the second bone piece of the bone piece pair are configured to provide, when approximated, a bone piece pair hidden engagement zone.

The above described and many other features and attendant advantages of embodiments of the present invention will become apparent and further understood by reference to the following detailed description when considered in conjunction with the accompanying drawings.

DETAILED DESCRIPTION OF THE INVENTION

Bone material for use in grafting is typically produced by various processes which may include debriding and removal of bone features such as bone shaft ends. There is no constraint as to which bone is actually used for a graft. In some instances, femurs and tibias are particularly desirable candidates for producing grafts, in part because these bones typically have a wall thickness that is greater than what is found on other types of bones.

Bone grafts can be prepared using any of a variety of techniques. For example, embodiments of the present invention include the manufacture of bone grafts using computer numerical control (CNC) machines, lathes, custom toolpaths and tooling, and the like. In some instances, particular graft embodiments may involve the use of custom cutters and/or jigs that are specifically designed for the manufacturing process. Tooling can be designed to provide desired production yields, speeds, and repeatability. This may involve various factors such as tooling changes, removing and installing new tooling or grafts, and set-up and tear down time.

In an exemplary manufacture process, a blank is cut from the bone, providing an operator with a useable piece of donor material. Often, such a piece is in the form of a square or block with a hole therethrough, for example in the middle of the piece. The graft piece can be cut or formed into its desired features using specific tooling and jigs. Many grafts have cancellous in the middle which serves as a bone growth stimulus. Osteoconductive or cancellous material may be introduced into the graft at any desired stage of the production process.

In some cases, techniques involve mechanically combining a multiple number of smaller bone pieces to create a larger piece. Optionally, such production processes may be accomplished without the use of medical device parts such as metal screws, pins, or plates. In some instances, production methods do not involve significant changes to CNC machine or tooling configurations, provide enhanced usage of donor tissue during processing and post processing, and provide desirable processing speeds. In some cases, purified collagen, calcium phosphate ceramics, or other osteoconductive materials may be used in conjunction with multiple bone pieces when preparing or implanting a bone graft assembly. In some cases, osteoinductive materials may be used in conjunction with multiple bone pieces when preparing or implanting a bone graft assembly. Exemplary osteoconductive materials may include demineralized bone matrix, stem cell products, and the like.

Figure 1:
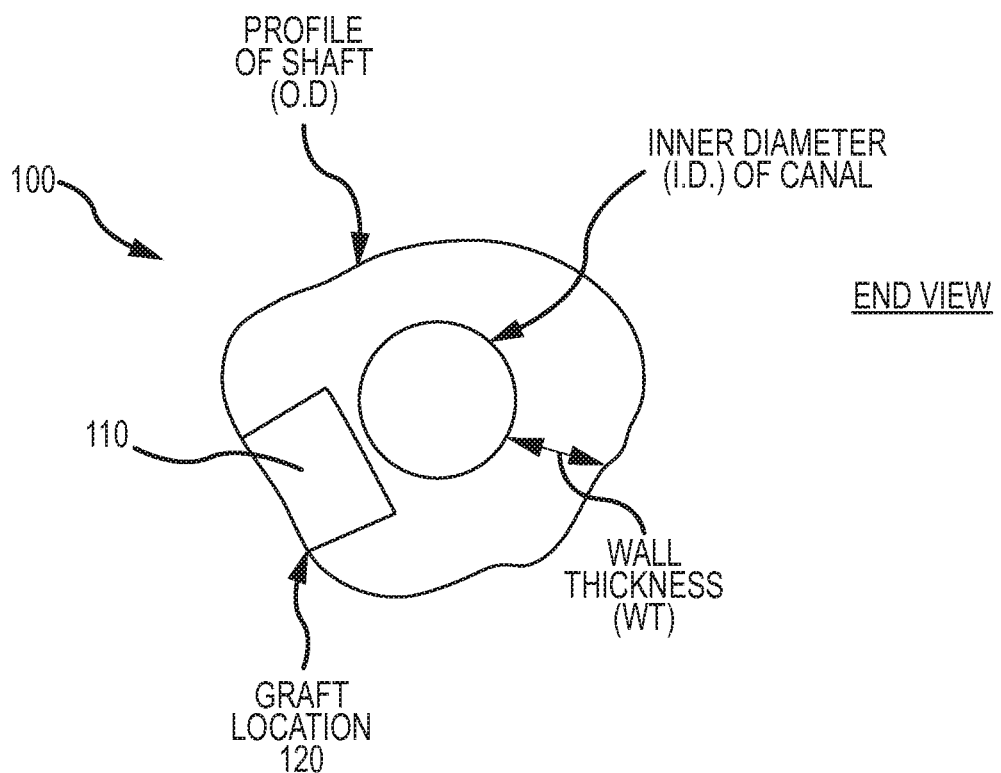
FIGS. 1, 1A, and 1B depict aspects of bone graft assemblies, their use, and/or manufacture, according to embodiments of the present invention.
Figure 1:
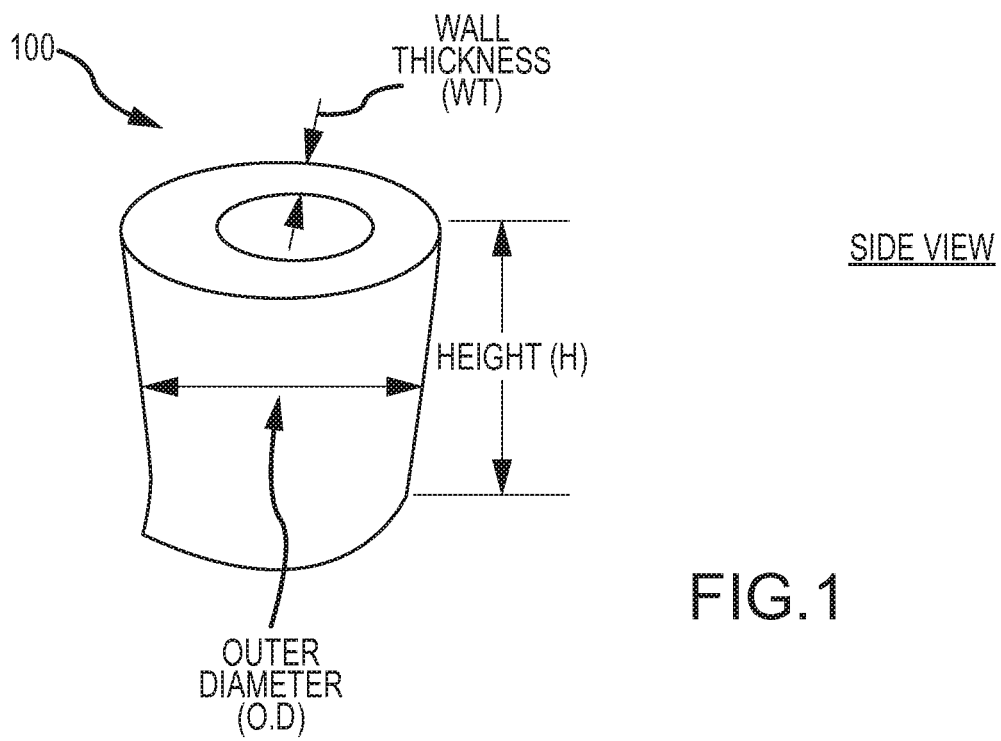

Turning now to the drawings, FIG. 1 illustrates aspects of a bone processing technique according to embodiments of the present invention. As shown here, a bone piece 100 (presented in both an end view and a side view) obtained from a bone shaft presents an outer profile or outer diameter (OD), an inner canal profile or diameter (ID), and a wall thickness (WT). A graft piece or blank 110 can be obtained from bone piece 100 from graft location 120. In some cases, the bone piece presents a cylindrical shape having a wall thickness (WT) of at least 6 mm. In some cases, the bone piece has a height (H) of at least 9 mm. Optionally, the bone piece may have a height of at least 15 mm. Any of a variety of tissue types, shapes, and sizes may be used to create a graft piece or blank.

Such graft pieces can be obtained or produced from any of a variety of bone material types, including fresh bone, fresh-frozen bone, freeze-dried bone, mineralized bone, demineralized bone, partially demineralized bone, and the like. In some instances, bone pieces can be obtained from any desired part of the skeleton, including without limitation the humerus, talus, femur, tibia, fibula, rib, pelvis, and the like.

Embodiments of the present invention encompass the use of multiple graft pieces or blanks for the manufacture of multi-piece graft compositions. In some instances, embodiments provide graft pieces that are easy to assembly but difficult to disassemble. In some cases, manufacturing methods involve the use of a minimal number of graft pieces to produce a multi-piece graft composition. Exemplary techniques also provide for the production of multi-piece grafts having desirable biomechanical and aesthetic characteristics.

Figure 1A:
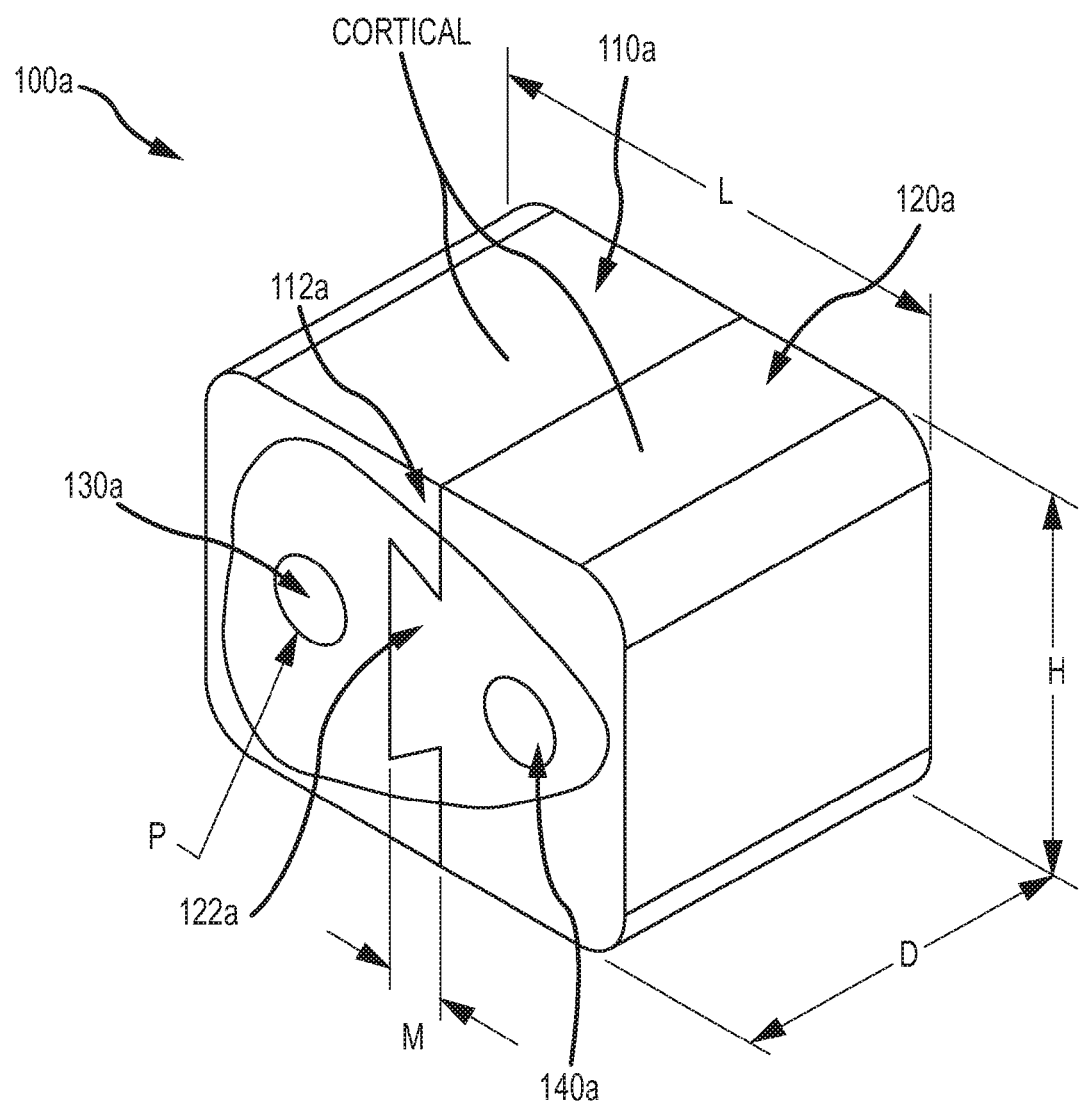

FIG. 1A illustrates an exemplary multi-piece bone graft assembly 100a according to embodiments of the present invention. Assembly 100a includes a first cortical (compact) bone piece 110a having a first dovetail 112a mating feature, and a second cortical bone piece 120a having a second dovetail 122a mating feature. Bone graft assembly 100a also includes a first cancellous (spongy) bone pin 130a disposed within the first cortical bone piece, and a second cancellous bone pin 140a disposed within the second cortical bone piece. The dovetail features (112a, 122a) can provide a press fit between the two pieces (110a, 120a). In some embodiments, the assembly 100a can have a first dimension L of about 14 mm, a second dimension D or about 10 mm, and a third dimension H or about 11 mm. In certain embodiments, the mating features can have a dimension M of about 1.59 mm. In certain embodiments, the pins may have a dimension or diameter P of about 2.39 mm. These dimensions may be varied or adjusted according to the use for which the assembly is intended. For example, the dimensions can be adjusted for appropriate use in a cervical spacer application, a vertebral spacer application, and the like.

Figure 1B:
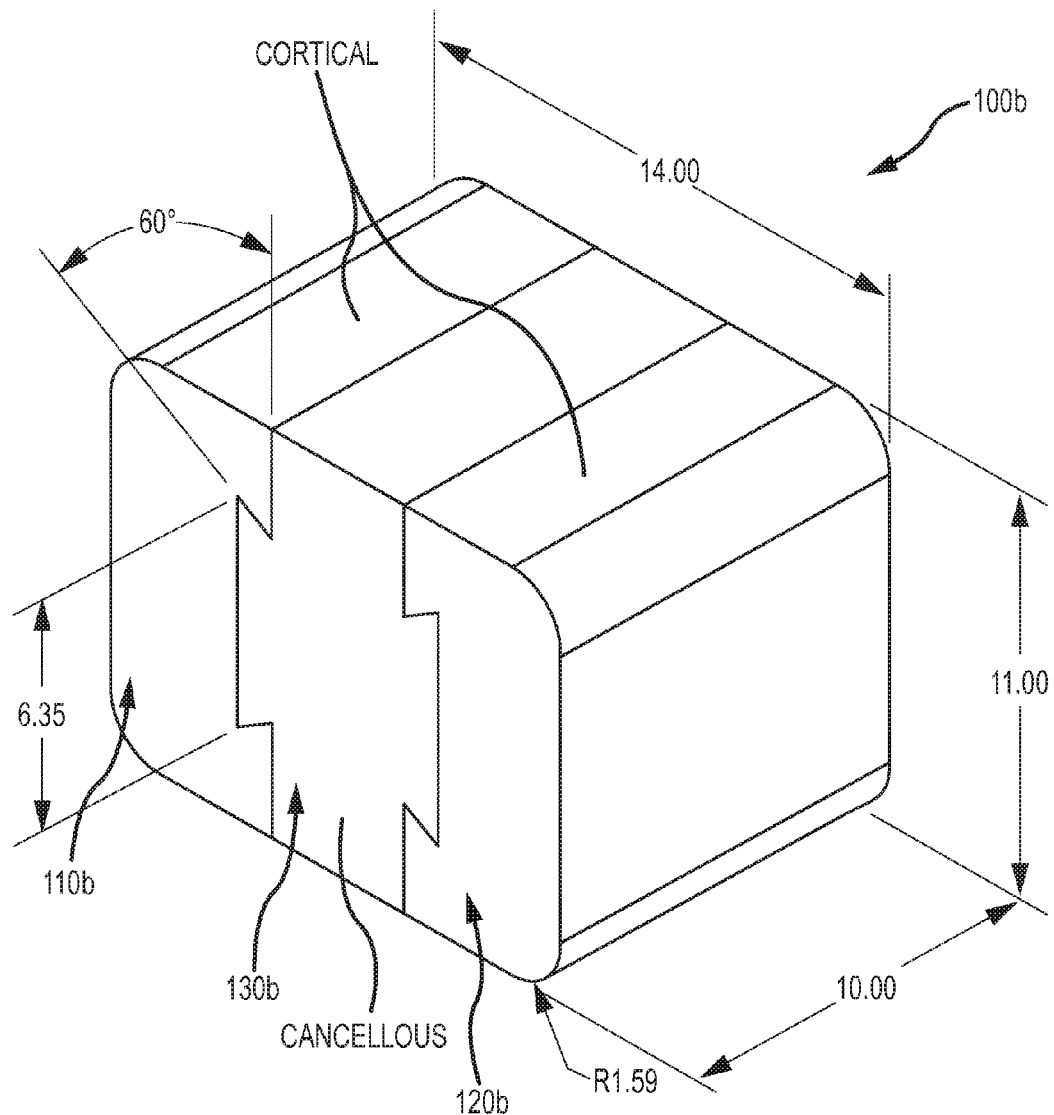

FIG. 1B illustrates an exemplary multi-piece bone graft assembly 100b according to embodiments of the present invention. Assembly 100b includes a first cortical bone piece 110b having a first dovetail mating feature (female), a second cortical bone piece 120b having a second dovetail mating feature (female), and a cancellous bone piece 130b having two dovetail mating features (male) disposed on opposing sides of the bone piece. The dovetail features can provide a press fit between the three pieces. The particular dimension values shown here (in millimeters) can be varied or adjusted according to the use for which the assembly is intended. For example, the dimensions can be adjusted for appropriate use in a cervical spacer application, a vertebral spacer application, and the like. In some cases, cancellous bone may be used for either or both of the first and second pieces. In some cases, cortical bone may be used for the third piece.

Figure 2A:
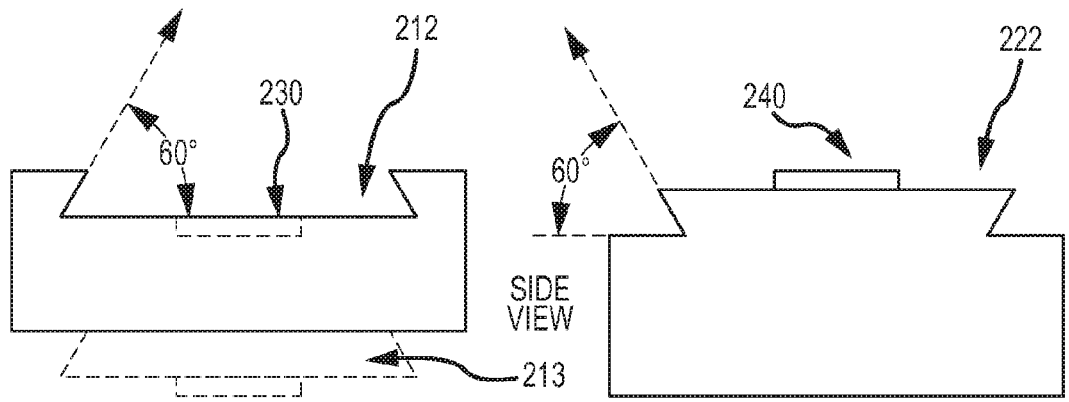
FIGS. 2A and 2B depict aspects of bone graft assemblies, their use, and/or manufacture, according to embodiments of the present invention.
Figure 2B:
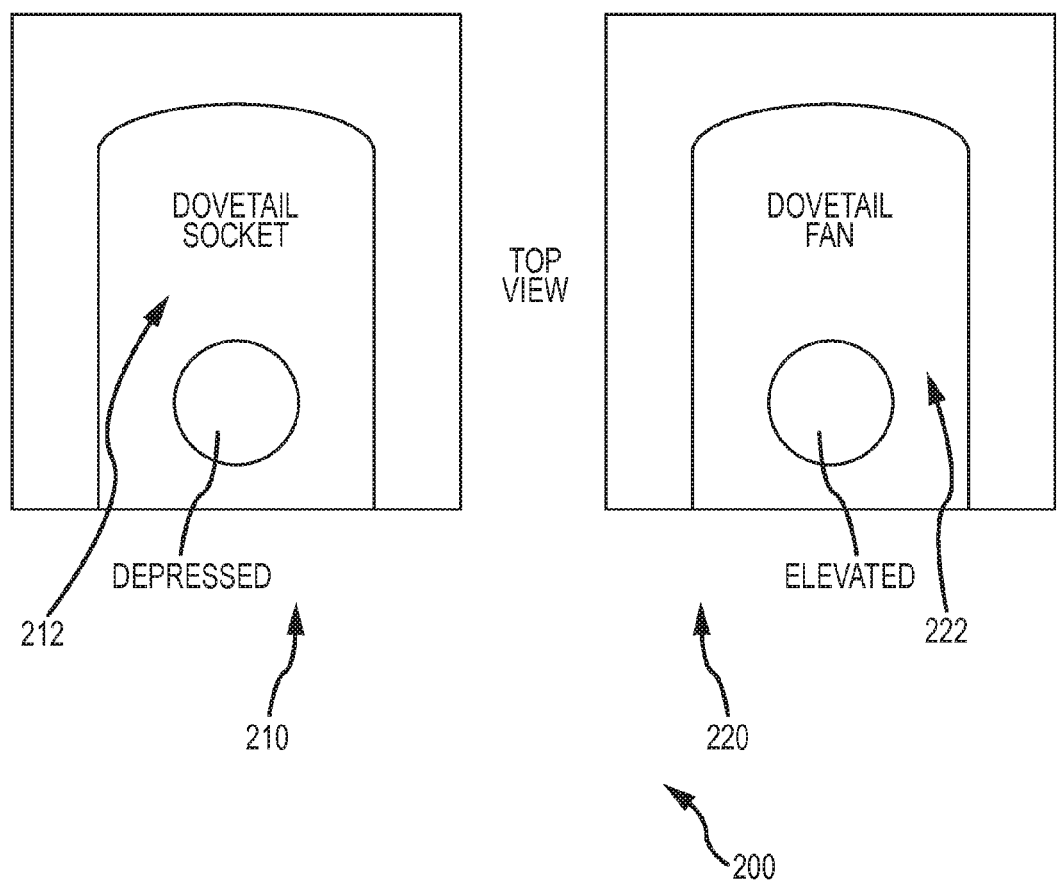

FIGS. 2A and 2B show aspects of an exemplary multi-piece bone graft assembly 200 according to embodiments of the present invention. Assembly 200 includes a first bone piece 210 having a first dovetail mating feature 212 (socket), and a second bone piece 220 having a second dovetail mating feature 222 (fan). As shown here, first bone piece 210 includes a depression or recess 230, and second bone piece includes a raised boss or spot 240. When the first and second bone pieces are combined, the dovetail features engage in a press fit, and the first piece recess 230 receives the second piece boss 240, so that the pieces snap and lock together. In some cases, a bone piece may include both a male dovetail feature (e.g. 213) and a female dovetail feature (e.g. 212), and in this way multiple pieces can be combined in a stacked configuration. Dovetail features can be configured in any of a variety of angled configurations (e.g. 60 degree angle, as shown here).

Figure 3:
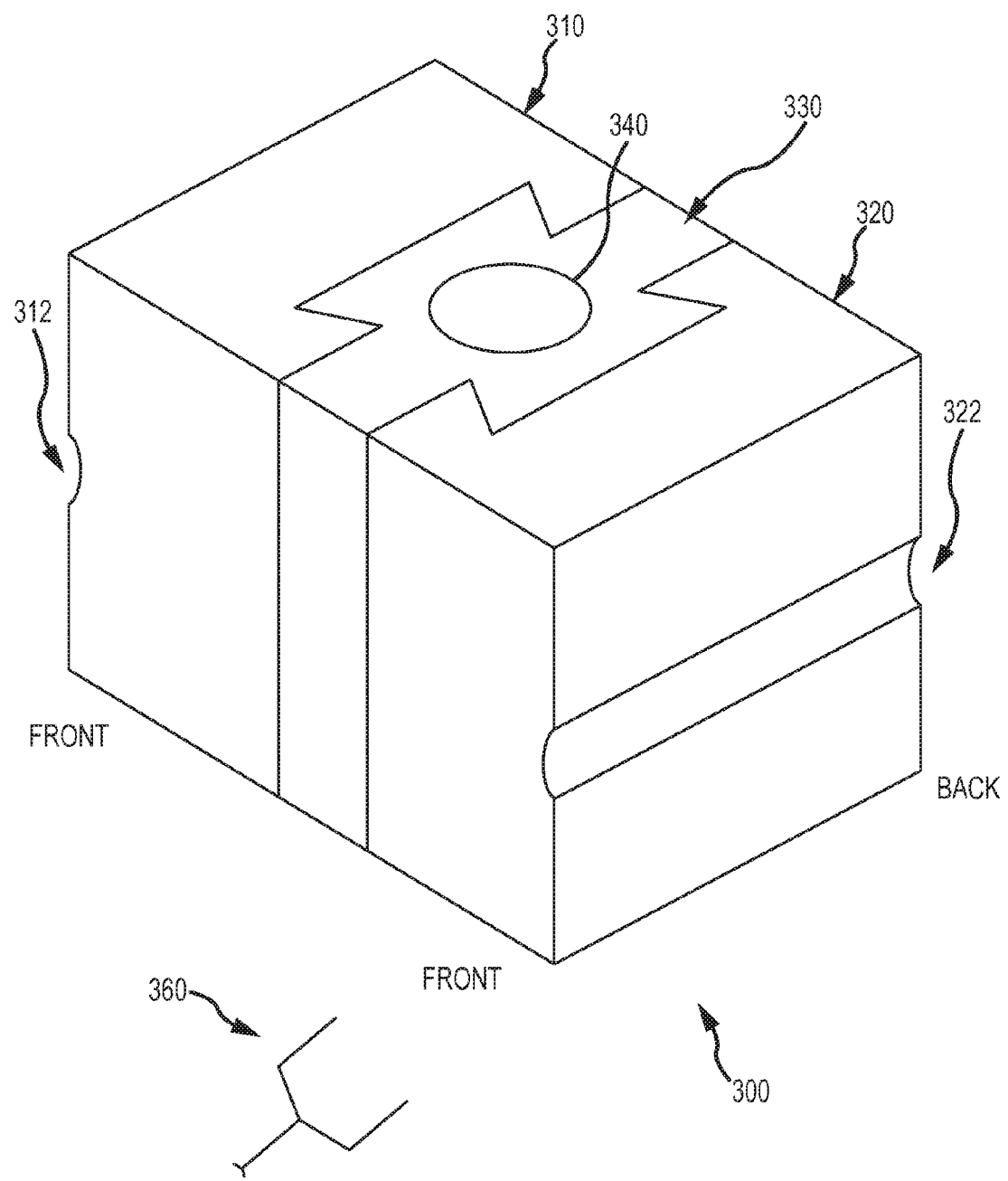
FIG. 3 depicts aspects of bone graft assemblies, their use, and/or manufacture, according to embodiments of the present invention.

FIG. 3 illustrates an exemplary multi-piece bone graft assembly 300 according to embodiments of the present invention. Assembly 300 includes a first cortical bone piece 310 having a first dovetail mating feature (socket), a second cortical bone piece 320 having a second dovetail mating feature (socket), and a third bone piece 330 having two dovetail mating features (fans) disposed on opposing sides of the piece. Bone graft assembly 300 also includes a bone pin 340 disposed within the third bone piece. Third bone piece 330 may include cortical or cancellous bone, for example. Similarly, bone pin 340 may also include cortical or cancellous bone. The dovetail features can provide a press fit between the three pieces. The pin may be configured as a plug, and optionally as a structural supporting or non-structural non-supporting element. One or more pieces of the assembly may include inserter slots configured for use with an inserting instrument or device. Hence, the bone graft assembly may be positioned within the patient's body using an introducer mechanism 360. As depicted here, first bone piece 310 includes an inserter slot 312 and second bone piece 320 includes an inserter slot 322. These slots can extend between the front side and the back side of the bone pieces.

Figure 4:
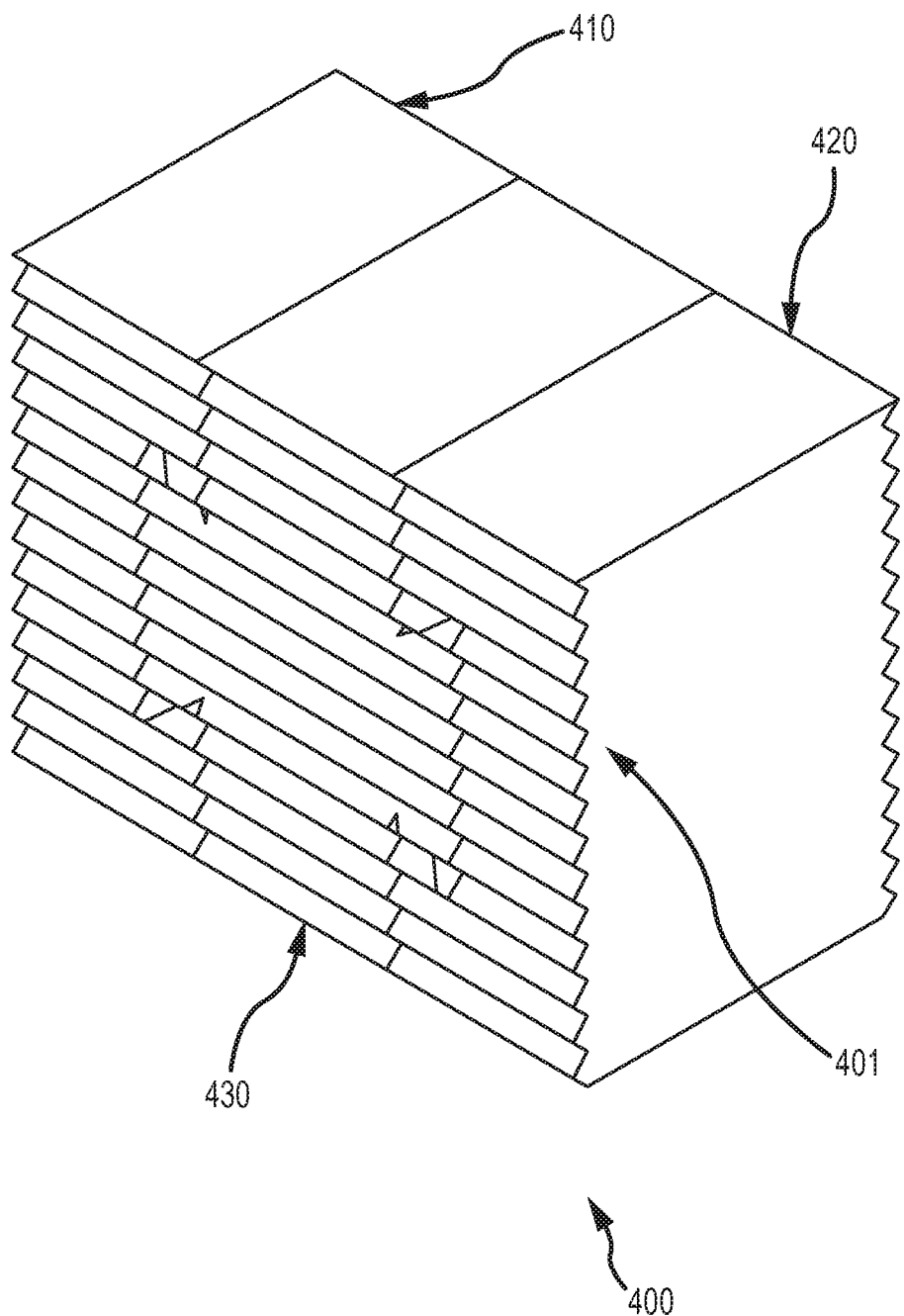
FIG. 4 depicts aspects of bone graft assemblies, their use, and/or manufacture, according to embodiments of the present invention.

FIG. 4 illustrates an exemplary multi-piece bone graft assembly 400 according to embodiments of the present invention. Assembly 400 includes a first cortical bone piece 410 having a first dovetail mating feature (female socket), a second cortical bone piece 420 having a second dovetail mating feature (female socket), and a cancellous bone piece 430 having two dovetail mating features (male fans) on opposing sides of the bone piece 430. The dovetail features can provide a press fit between the three pieces. As shown here, each of the pieces provide the graft assembly with surface ridges or corrugations 401.

Figure 5A:
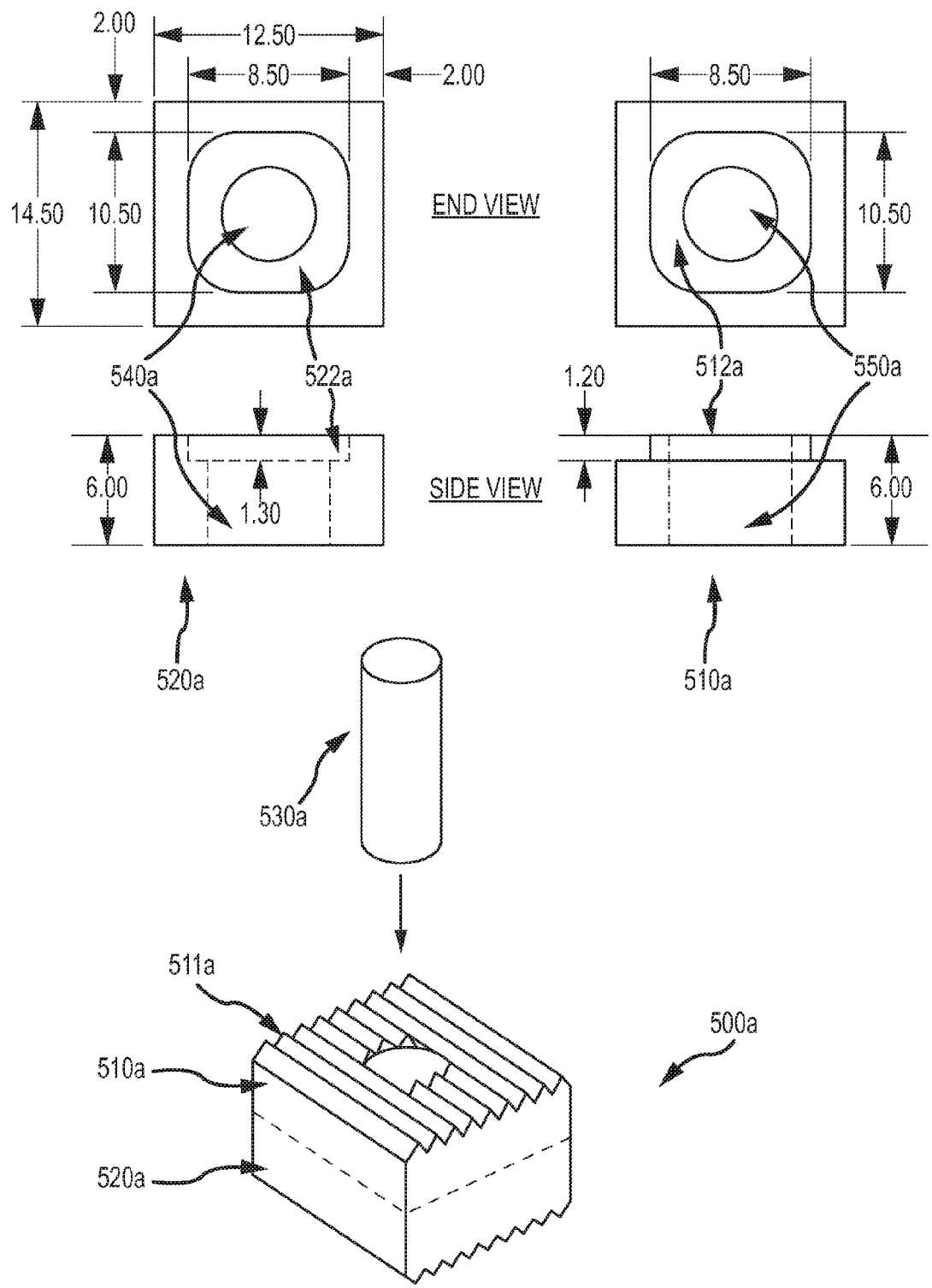
FIGS. 5A to 5D show aspects of bone graft assemblies, their use, and/or manufacture, according to embodiments of the present invention.

FIG. 5A illustrates an exemplary multi-piece bone graft assembly 500a according to embodiments of the present invention. Assembly 500a includes a first cortical bone piece 510a having a first mating feature or boss 512a, a second cortical bone piece 520a having a second mating feature or pocket 522a, and a cancellous pin or plug 530a that can be inserted through both the first and second cortical bone pieces via respective apertures (540a, 550a) in the first and second bone pieces. As shown here, the first and second bone pieces engage in such a way that the mating features are enclosed or hidden from view when the bone pieces are combined. This configuration provides a large amount of surface area for mating. Further, the pieces can be constructed without removing a significant amount of graft material from a donor bone. In some cases, the bone pieces can be constructed with a line to line tolerance. In some instances, first and/or second bone pieces may not each have an aperture therethrough. In some embodiments, purified collagen, calcium phosphate ceramics, or other osteoconductive materials may be placed within apertures or holes of the bone pieces. This approach can be used to stack any desired number of bone pieces together. One or more surface of the bone pieces may include ridges or corrugations (e.g. 511a). The dimensions depicted here (in millimeters) may be varied or adjusted according to the use for which the assembly is intended. For example, the dimensions can be adjusted for appropriate use in a cervical spacer application, a vertebral spacer application, and the like.

Hence, as depicted here, two graft pieces can be joined together using a male boss or ridge (512a) and a female hole or recess 522a), thus providing an interference or press fit. Both male and female features can have the same contour shape as its mating counterpart. In some cases, a size differential between the components can create interference which resists separation. In some instances, such graft pieces can be joined together using a male boss and a female pocket interference or press fit, such that both male and female features have the same contour shape as its mating counterpart, and the combined graft assembly presents an outside profile of a cervical graft shape. A size differential between the components or mating features can create an interference that resists separation.

A cervical spacer bone graft assembly having features similar to those of FIG. 5A was tested in comparison with a monolithic spacer. The observed Compression Averages (N) for a monolithic structure and bone graft (multi-piece) assembly were 15,000 and 13,200, respectively. Hence, the multi-piece features of the bone graft assembly were not observed to have a significant effect on compression properties as compared to a monolithic structure. Moreover, as explained in Patwardhan et al., *Load-carrying capacity of the human cervical spine in compression is increased under a follower load*, Spine 2000 Jun. 15; 25(12):1548-54, the content of which is incorporated herein by reference, the compressive load on the human cervical spine is estimated to range from 120 to 1200 N during activities of daily living. Hence, the tested graft assembly provides more than sufficient load strength for an implant.

Figure 5B:
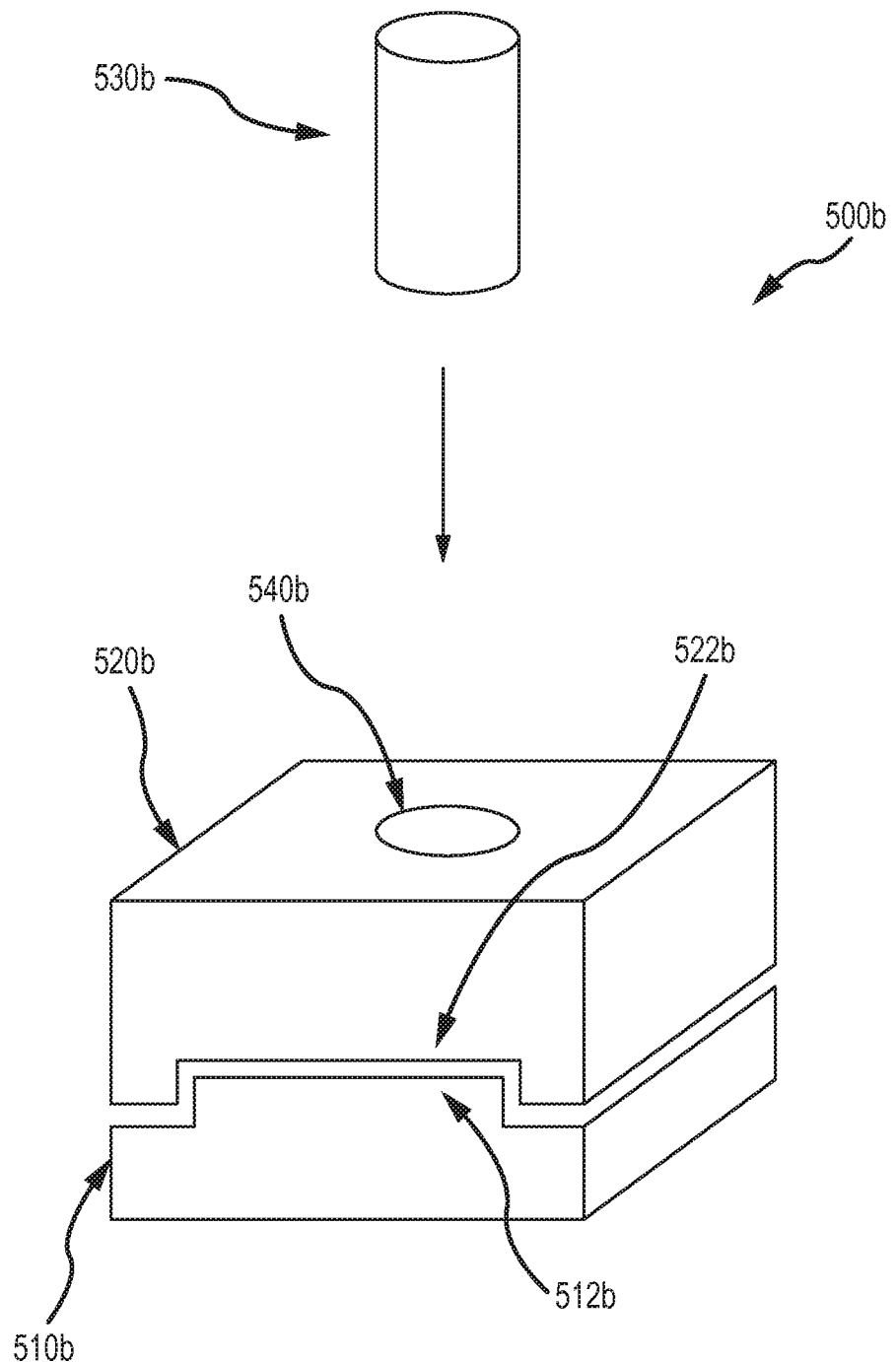

FIG. 5B illustrates an exemplary multi-piece bone graft assembly 500b according to embodiments of the present invention. Assembly 500b includes a first cortical bone piece 510b having a first mating feature or boss 512b, a second cortical bone piece 520b having a second mating feature or pocket 522b, and a cancellous pin 530b or plug that can be inserted through both the first and second cortical bone pieces via an aperture 540b of the combined assembly. As shown here, the first and second bone pieces can be combined in a sliding fashion, by slipping the pieces together for example. Optionally, the first and second bone pieces can be engaged via a press fit.

Figure 5C:
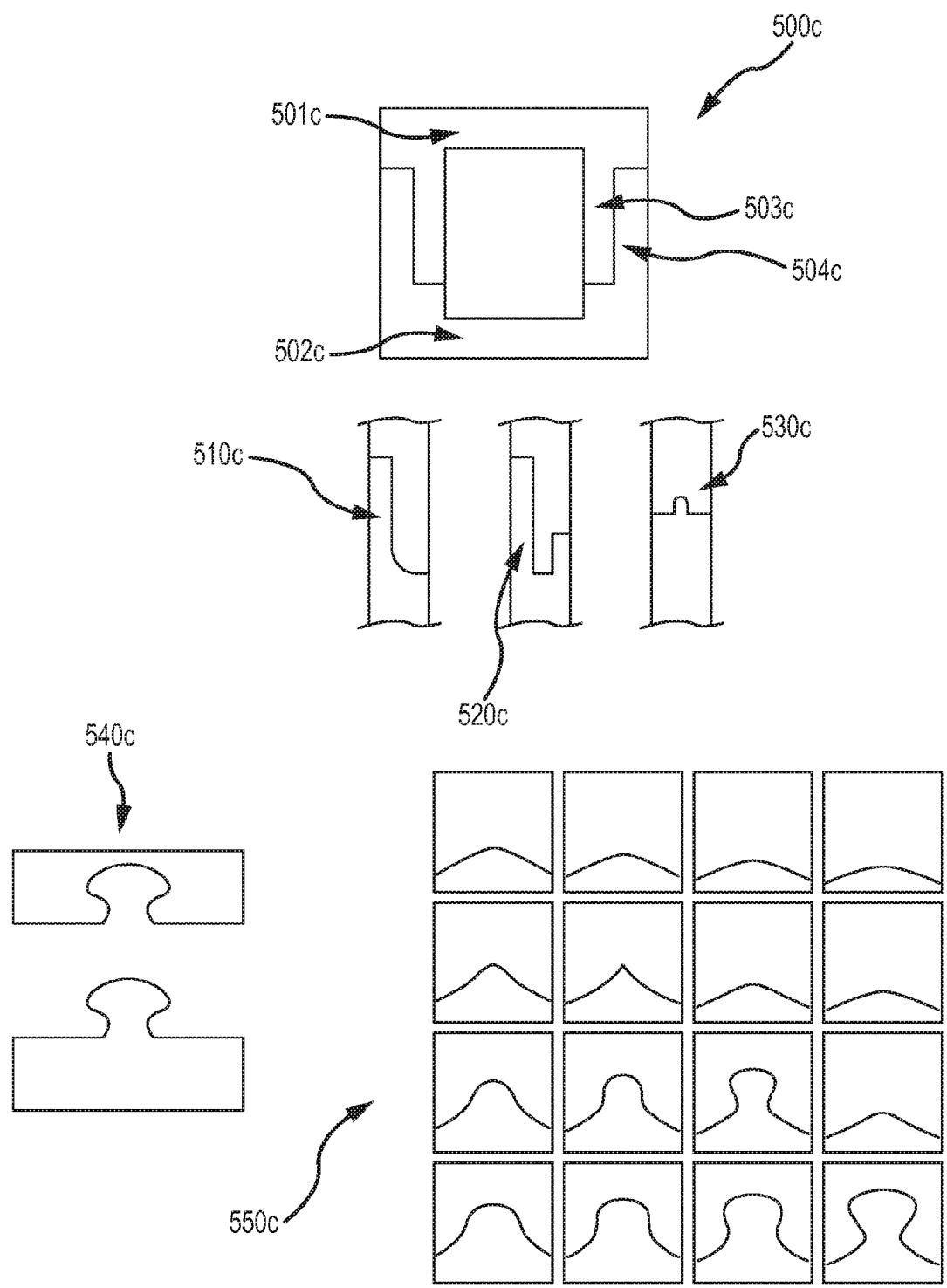

As depicted in FIG. 5C, pocket designs for bone graft assemblies can be configured in any of a variety of shapes and sizes. For example, as shown here, bone assembly 500c includes a first bone piece 501c and a second bone piece 502c, each of the bone pieces including a respective mating feature (503c, 504c). In some cases, a pocket cross-section can include a curved shape or portion (510c), a notched shape or portion (520c), or a ridge shape or portion (530c), or a puzzle shape or portion (540c), or any of a variety of curved or elliptical shapes or portions (550c). Hence, male and female assemblies can complement each their respective shapes. For example, a male mating feature may have a curved shape that is complementary to a curved shape of a female mating feature. Similarly, a male mating feature may have a linear shape that is complementary to a linear shape of a female mating feature. In some cases, male and female mating features may have shapes with combined curved and linear portions. It is also understood that in some cases, a first mating feature may include a combination of male and female features, and a second mating feature may include a combination of corresponding female and male features. Often, interference between mating features can be achieved via size differential, or a shape differential as described elsewhere herein.

Figure 5D:
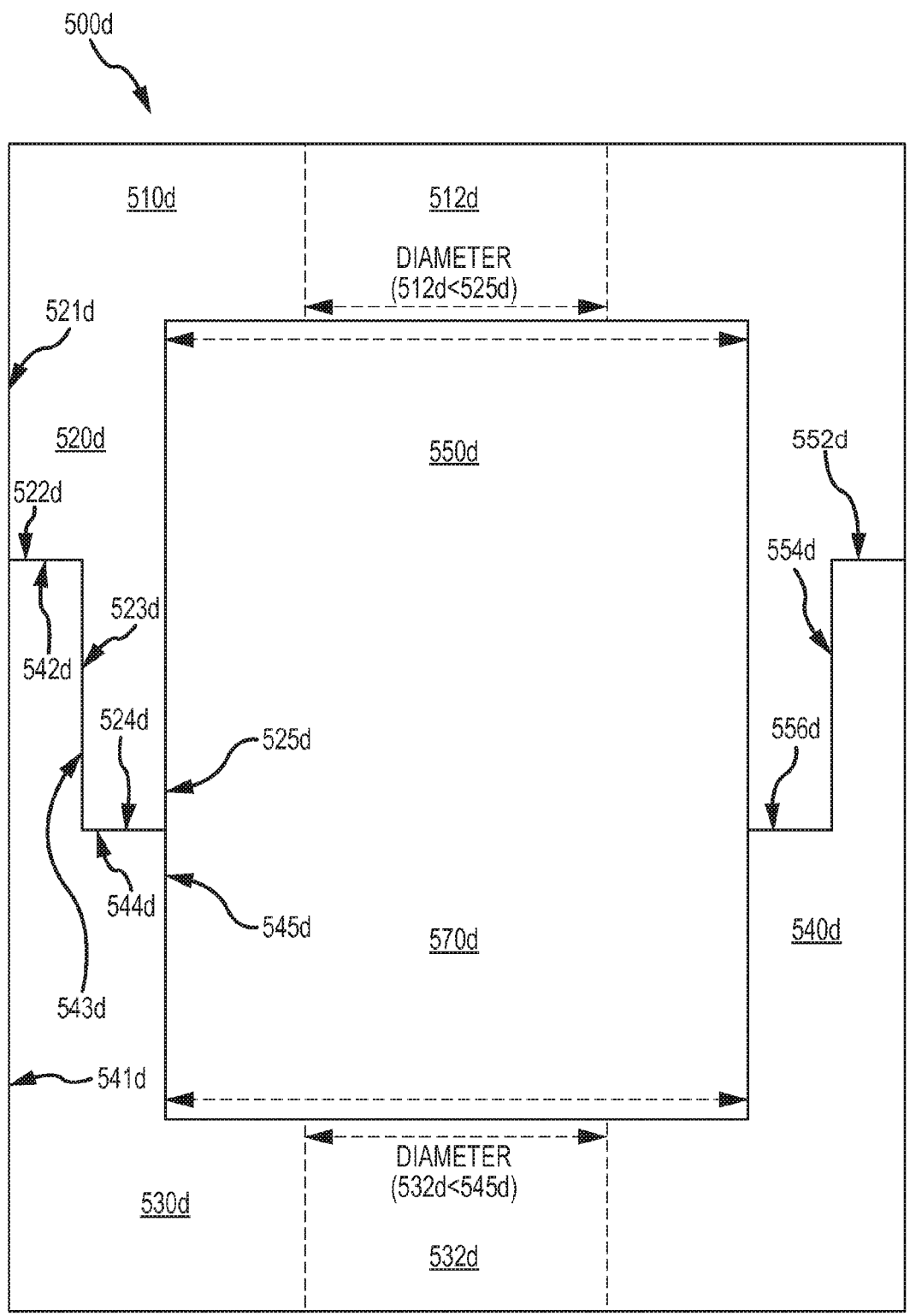

FIG. 5D depicts an exemplary bone graft assembly 500d according to embodiments of the present invention. As shown here, the bone graft assembly includes a first bone piece 510d having a first mating feature 520d, and a second bone piece 530d having a second mating feature 540d. The first and second mating features are configured to provide, when approximated, a hidden engagement zone 550d. The hidden engagement zone 550d can include, for example, a peripheral engagement zone 552d, a medial engagement zone 554d, and an inner engagement zone 556d. In some instances, the first mating feature 520d includes an outer surface 521d, a peripheral surface 522d, a medial surface 523d, an inner surface 524d, and a core surface 525d. In some instances, the second mating feature 540d includes an outer surface 541d, a peripheral surface 542d, a medial engagement surface 543d, an inner surface 544d, and a core surface 545d. The first and second mating features can be configured to provide, when approximated, a peripheral engagement zone 552d defined between at least portions of the peripheral surfaces (522d, 542d) of the first and second mating features, respectively, a medial engagement zone 554d defined between at least portions of the medial surfaces (523d, 543d) of the first and second mating features, respectively, and an inner engagement zone 556d defined between at least portions of the inner surfaces (524d, 545d) of the first and second mating features, respectively. The inner engagement zone 556d can be disposed interior to the medial engagement zone 554d. The medial engagement zone 554d can be disposed interior to the peripheral engagement zone 552d. In some case, at least a portion of the medial engagement zone 554d is disposed between the core surface 525d of the first mating feature and the outer surface 541d of the second mating feature. As shown here, the first bone piece 510d includes a first aperture 512d having a diameter or dimension, and a first core surface 525d defining a diameter or dimension. The diameter or dimension of the first core surface 525d is greater than the diameter or the dimension of the first aperture 512d. Relatedly, the second bone piece 530d includes a second aperture 532d having a diameter or dimension, and a second core surface 545d defining a diameter or dimension. The diameter or dimension of the second core surface 545d is greater than the diameter or dimension of the second aperture 532d. In some instances, the diameters or dimensions of the first and second core surfaces are the same or substantially the same. In some instances, the diameters or dimensions of the first and second apertures are the same or substantially the same. In some instances, a size differential between the first aperture and first core surface, and/or between the second aperture and the second core surface, provide a bone graft assembly with an inner chamber area 570d.

In some instances, the first and second mating features are configured to provide, when approximated, a continuous aperture that extends through the first and second bone pieces of the assembly. In some instances, the continuous aperture is at least partially defined by the first and second mating features. In some instances, the continuous aperture is not at least partially defined by the first and second mating features. In some instances, the first mating feature includes an annular wall disposed between the first mating feature medial and core surfaces, and the second mating feature includes a second annular wall disposed between the second mating feature medial and outer surfaces. Optionally, the second annular wall can be configured to slidingly receive the first annular wall. In some instances, the first and second mating features are configured to provide, when approximated, a press fit at the medial engagement zone.

Figure 6:
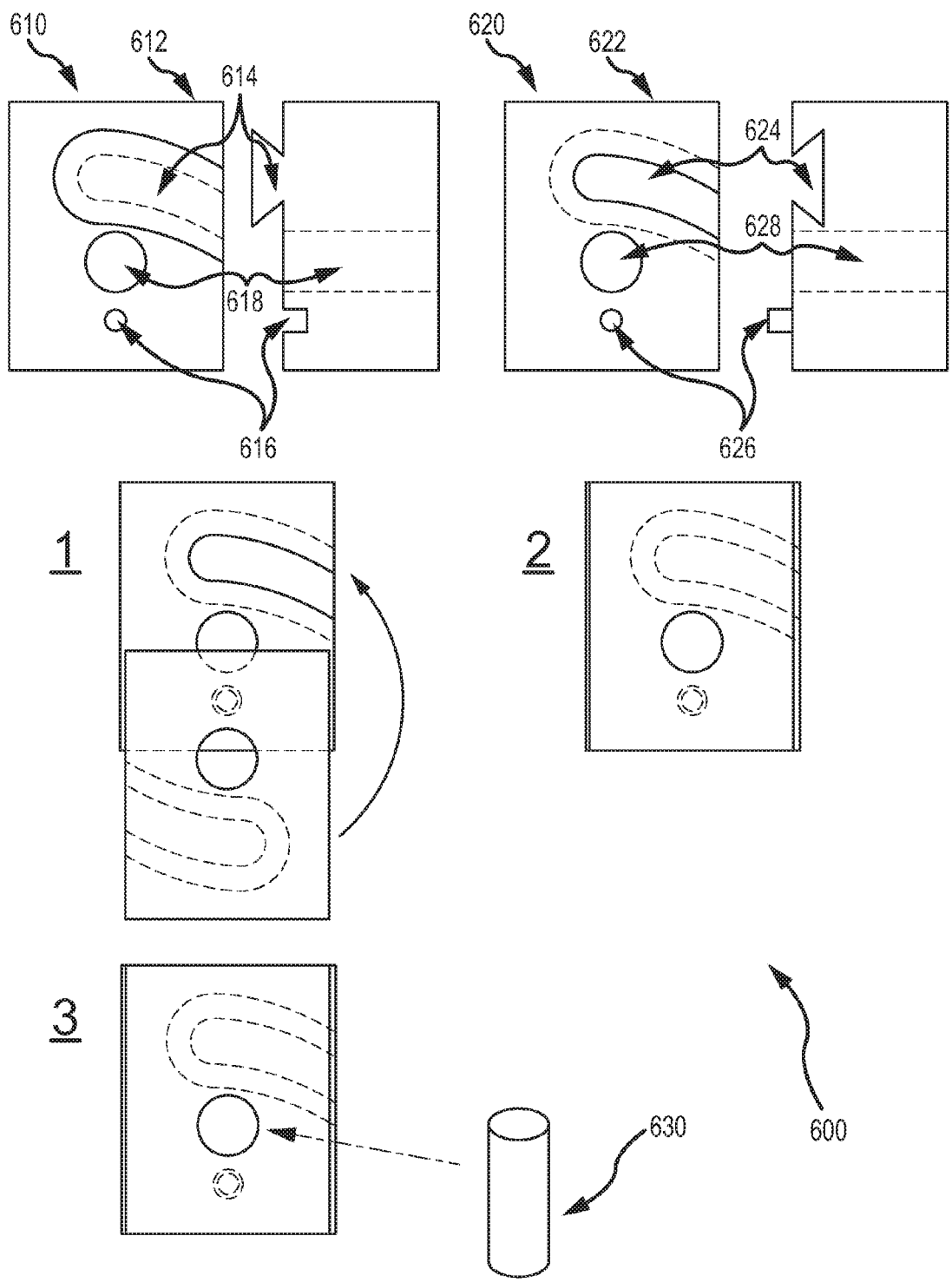
FIG. 6 depicts aspects of bone graft assemblies, their use, and/or manufacture, according to embodiments of the present invention.

FIG. 6 illustrates an exemplary multi-piece bone graft assembly 600 according to embodiments of the present invention. Assembly 600 includes a first cortical bone piece 610 having a first mating feature 612 and an aperture 618, a second cortical bone piece 620 having a second mating feature 622 and an aperture 628, and a cancellous pin or plug 630 that can be inserted through both the first and second cortical bone pieces. As shown here, the first mating feature 612 includes a raised ridge 614 and a pocket 616. The second mating feature 622 includes a channel 624 configured to receive ridge 614, and a pin 626. Pocket 616 of first mating feature is configured to receive pin 626 of second mating feature (e.g. so as to provide a pivot between the first and second bone pieces). This embodiment presents a dovetail J-lock design, whereby the ridge 614 and recess 624 engage as a light press fit, and the pin 626 and pocket 616 engage as a slip fit. The cancellous plug 630 is inserted through the first and second bone pieces (e.g. via apertures 618, 628), and thereby operates as a lock, so as to prevent or inhibit the first and second pieces from rotating relative to each other (e.g. about pivot provided by pin 626 and pocket 616. In the assembly process, shown here, step 1 includes placing the pin 626 in the pocket 616 (e.g. so as to provide a pivot), step 2 includes rotating the bone pieces relative to one another about the pivot, so that channel 624 receives ridge 614, and step 3 includes placing the plug 630 in the apertures (618, 628). In some instances, one or both of the bone pieces may include teeth.

Figure 7:
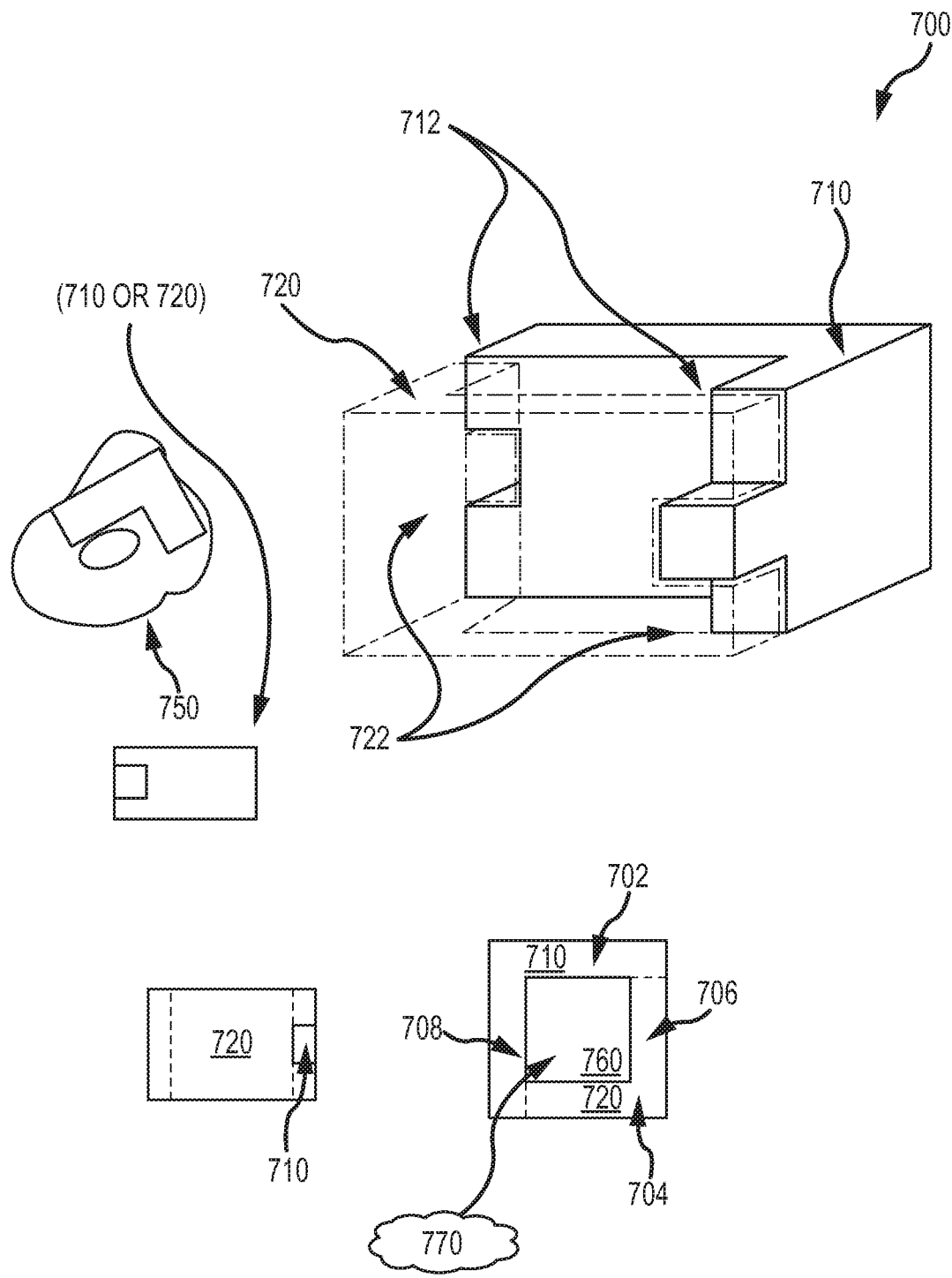
FIG. 7 depicts aspects of bone graft assemblies, their use, and/or manufacture, according to embodiments of the present invention.

FIG. 7 illustrates an exemplary multi-piece bone graft assembly 700 according to embodiments of the present invention. Assembly 700 includes a first cortical bone piece 710 having a first mating feature 712, a second cortical bone piece 720 (shown transparently) having a second mating feature 722. The embodiment depicted here presents a box dovetail design.

The first and second mating features (712, 722) can engage in a medium press fit. As shown here, first and second bone pieces can have the same shape, and can be obtained from a donor bone segment 750 as shown in FIG. 7A. In this way, cortical walls of the graft assembly can be constructed by building the walls separately. For example, a graft assembly may present an open box shape, and include a posterior wall 702, an anterior wall 704, and two opposing side walls (706, 708). In some embodiments, each of the walls may be formed of a distinct and separate piece. A cancellous plug or cancellous material 740 can be placed within a central portion or area 760 defined by first and second cortical bone pieces. For example, a cancellous plug or cancellous material 770 can be placed within one or more open box shape assemblies as described above.

Figure 8:
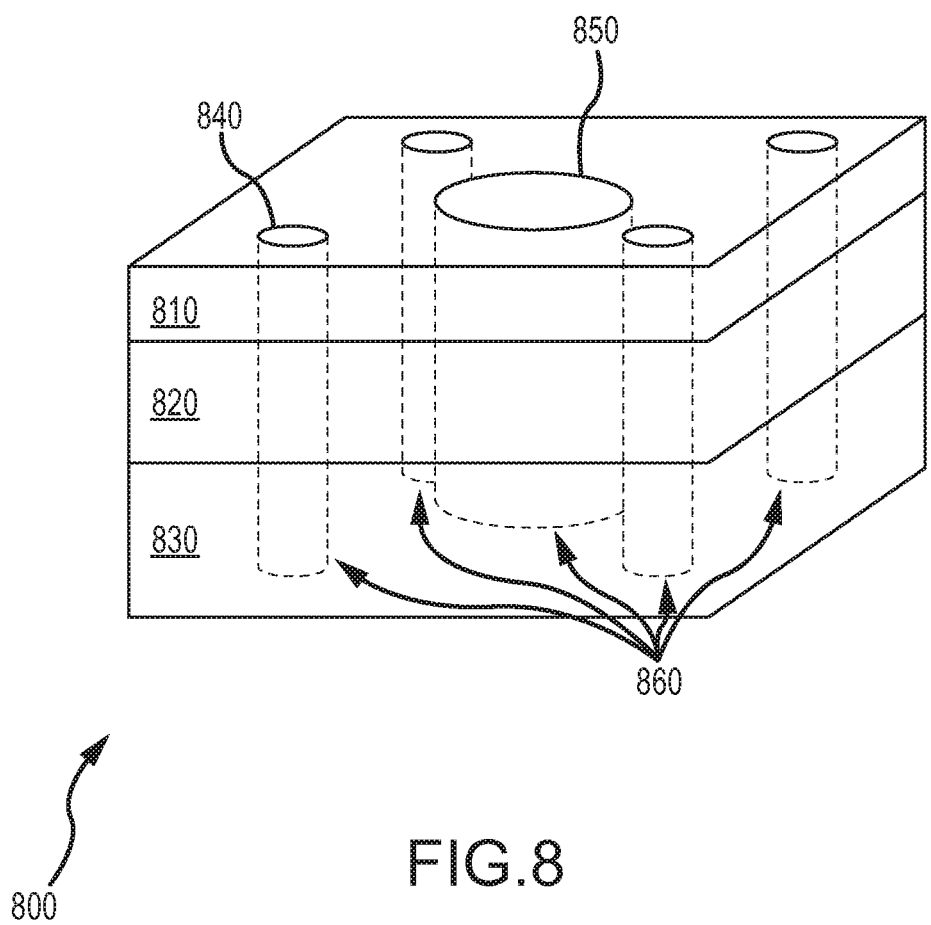
FIG. 8 depicts aspects of bone graft assemblies, their use, and/or manufacture, according to embodiments of the present invention.

FIG. 8 illustrates an exemplary multi-piece bone graft assembly 800 according to embodiments of the present invention. Assembly 800 includes a first cortical bone piece 810, a second cortical bone piece 820, and a third cortical bone piece 830. The cortical bone pieces can be combined in a stacked configuration, such that the second bone piece 820 is disposed between the first and third bone pieces (810, 830). In some embodiments, an assembly may also include pins or plug. For example, as shown here, assembly 800 includes two or more cortical bone pins 840 and one cancellous bone plug 850. The pins and plugs are disposed within the first, second, and third bone pieces (e.g. via respective apertures 860 extending through pieces of the bone graft assembly). The cortical bone pins operate to secure the bone pieces together. This design can be used to stack any desired number of bone pieces together. Optionally, the central cancellous plug can be configured as a pin.

Figure 9:
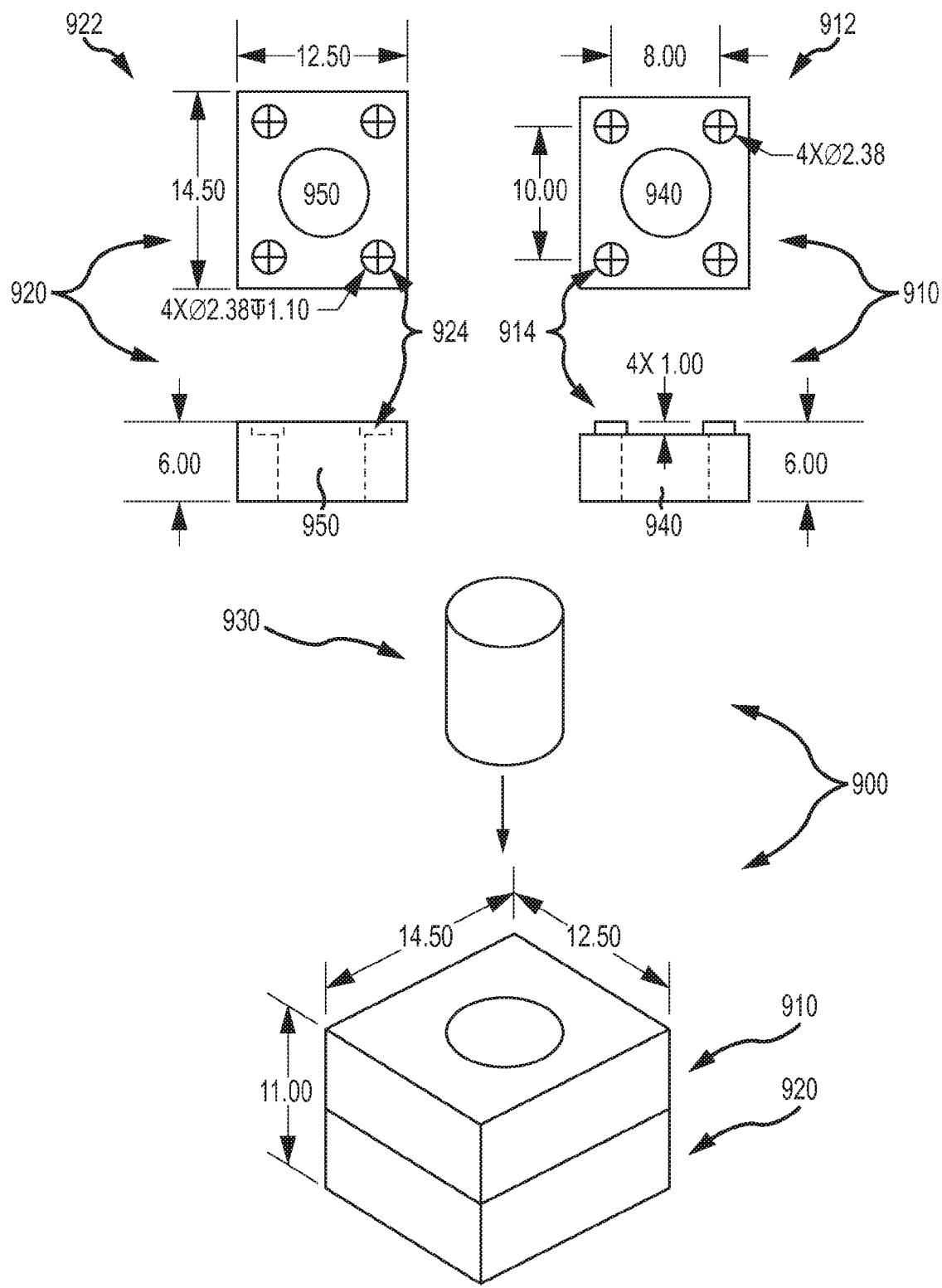
FIG. 9 depicts aspects of bone graft assemblies, their use, and/or manufacture, according to embodiments of the present invention.

FIG. 9 illustrates an exemplary multi-piece bone graft assembly 900 according to embodiments of the present invention. Assembly 900 includes a first cortical bone piece 910 having a first mating feature 912 with multiple bosses or buttons 914, a second cortical bone piece 920 having a second mating feature 922 with multiple pockets or recesses 924 configured to receive the bosses. The bosses can be pressed into the pockets, so as to hold the first and second graft pieces together. This configuration provides a large amount of surface area for mating, and the mating feature is hidden. Further, the pieces can be constructed without removing a significant amount of graft material. According to some embodiments, the first and second bone pieces can be provided in a universal design configuration, wherein the first bone piece has a combination of bosses and pockets (e.g. two bosses and two pockets), and the second piece has a combination of bosses and pockets (e.g. two bosses and two pockets). Hence, in some instances, two bone pieces, each having the same shape, can be joined to form a bone graft assembly. In some instances, the bone pieces can be constructed with a 0.00 (or line to line toolpath) tolerance press, providing a snap-like fit. The dimensions depicted here (in millimeters) may be varied or adjusted according to the use for which the assembly is intended. For example, the dimensions can be adjusted for appropriate use in a cervical spacer application, a vertebral spacer application, and the like. In some instances, assembly 900 may also include a pin or plug 930 (e.g. that includes cancellous bone material) that extends through corresponding apertures (940, 950) in the first and second bone pieces.

Hence, two graft pieces can be joined together by creating a round female hole on one piece and a corresponding round boss on the other piece. When the two graft pieces are pressed together, a uniform interference fit is formed. In some cases, a first graft piece includes one or more bosses, and a second graft piece includes one or more corresponding recesses. In some cases, as described elsewhere herein, the first graft piece can include a combination of bosses and recesses, and the second graft piece can include a corresponding combination of recesses and bosses. In this way, the configuration can present a universal blank or graft piece, where a single shape can function as both the first piece and the second piece. In addition to circular or round boss shapes, graft pieces according to embodiments of the present invention may be configured to present any desired curved or non-linear boss shape.

Figure 10:
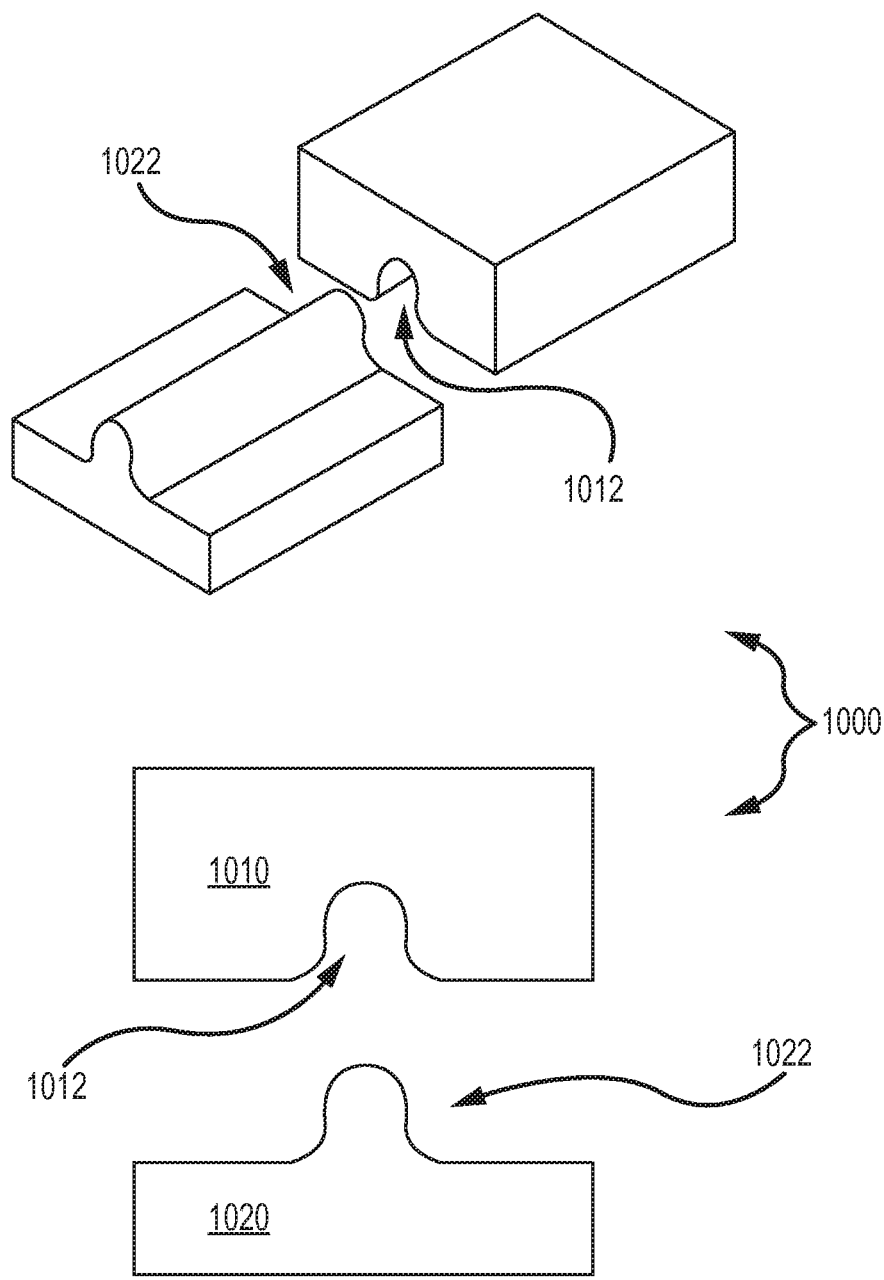
FIG. 10 depicts aspects of bone graft assemblies, their use, and/or manufacture, according to embodiments of the present invention.

FIG. 10 illustrates an exemplary multi-piece bone graft assembly 1000 according to embodiments of the present invention. Assembly 1000 includes a first cortical bone piece 1010 having a first mating feature or channel 1012, a second cortical bone piece 1020 having a second mating feature or ridge 1022. The first and second bone pieces can be engaged by sliding the ridge along the channel, or by pressing the bone pieces together. First and second bone pieces can include cortical bone material, for example. In some cases, the pieces can be joined by a press fit, with a line to line or 0 tolerance. The configuration shown in FIG. 10 provides a strong fit. An axial cross-section is also depicted. An exemplary method of preparing such a bone graft assembly may include cutting blank profiles, press the blanks together, cutting or adding the outer and inner profiles or inserter features at the same time or separately, adding cancellous or other material, and adding surface ridges or features.

Bone pieces can be created using any desired toolpaths and feed rates. In some instances, a feed rate can be within a range between about 10 in/min to about 30 in/min.

In some instances, contraction due to lyophilization may increase separation resistance in combination with press-fitting. In some instances, it is possible to machine two graft pieces, and then heat one piece, and/or cool an adjoining piece, so that there is less interference when joined, but upon returning to room or body temperature the interference between the two pieces increases.

Non-Uniform Press Fits

According to some embodiments of the present invention, a mating feature of a first bone piece can have a shape that is non-complimentary to a shape of a mating feature of a second bone piece. Hence, an interface between the first and second mating features can be defined by a non-uniform press fit. In some cases, the first mating feature can present a polygon shape, and the second mating feature can present a curved shape. In some cases, mating features can present two polygons, e.g. two hexagons, offset by 45 degrees. In some cases, mating features can present hexagon and octagon combinations. In some cases, mating features can present any of a variety of polygons, curved shapes such as ovals, ellipses, or circles, enclosed splines, irregular amoeba-like shapes, and the like. In some cases, polygonal shapes may have rounded corners, which can be formed by rounded endmill tools.

Figure 11:
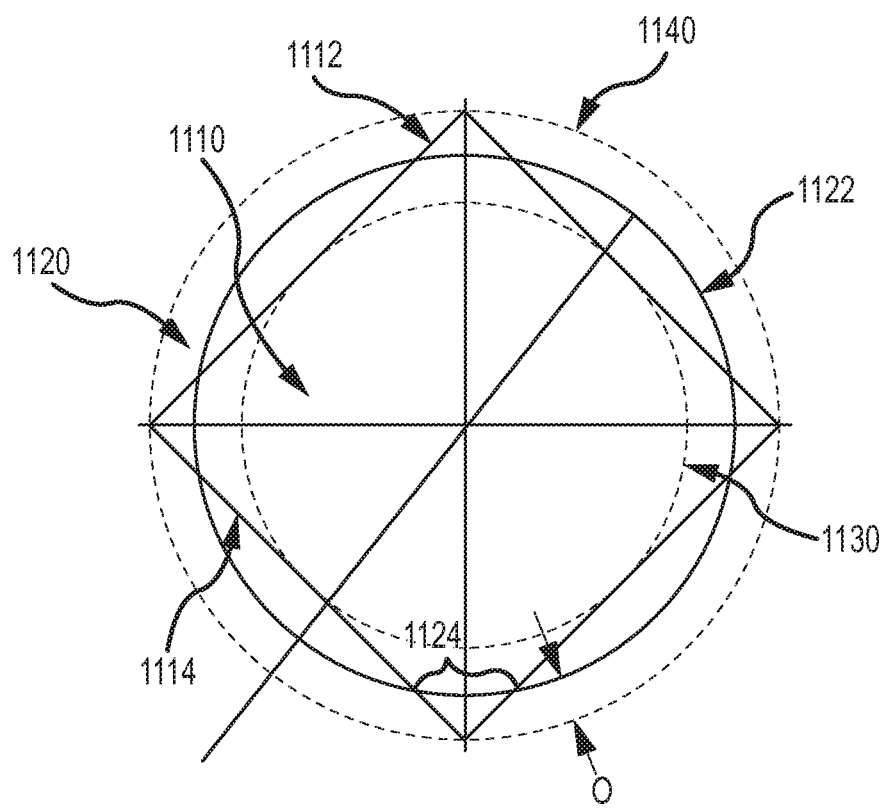
FIG. 11 depicts aspects of bone graft assemblies, their use, and/or manufacture, according to embodiments of the present invention.

As shown in FIG. 11, the corners or angles 1112 of a square shaped mating feature 1110 (e.g. boss) can operate as a biting feature, when pressed together with a round shaped mating feature 1120 (e.g. pocket). When pressing the bone pieces together, the corners 1112 of the square peg or boss provide a greater press fit than the other parts of the square peg (e.g. the edges, or sides 1114). Such configurations provide a firm and sturdy fit that is relatively easy to press and also difficult to remove. In the embodiment shown here, the outer diameter 1122 of the round pocket 1120 is circumscribed about a circle (1122) that is halfway between a first circle 1130 tangent to the sides of the polygon and a second circle 1140 that intersects the apexes of the polygon. In some cases, the radial overlap O may be about 0.008 inches. In some instances, other radial overlap distances O may be used. Hence, as shown here, the biting edge 1112 can extend into the circle shape to the extent of the radial overlap O distance. For example, when the first and second bone pieces are pressed together, a corner segment 1112 of the boss and an arc segment 1124 of the pocket can be pressed together.

Figure 12:
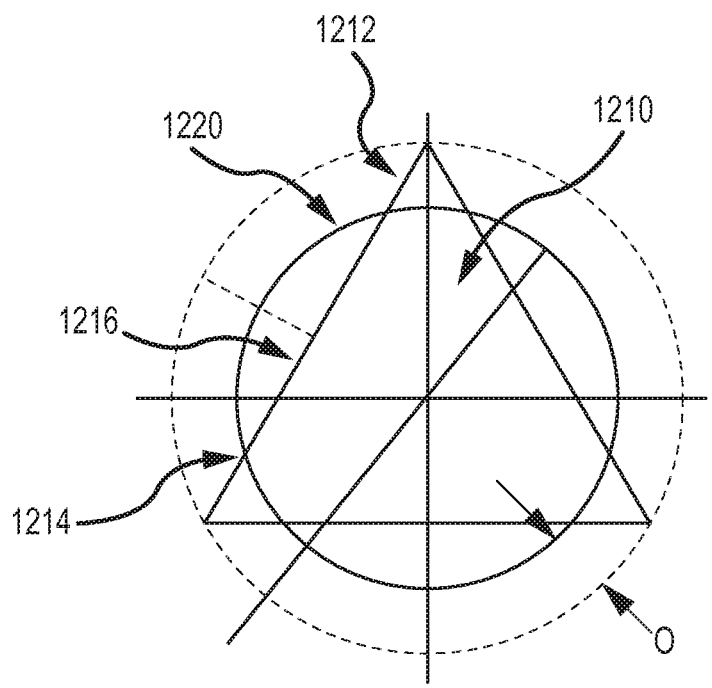
FIG. 12 depicts aspects of bone graft assemblies, their use, and/or manufacture, according to embodiments of the present invention.

FIG. 12 presents a related configuration, where the first bone piece has a first mating feature (e.g. a pine) with a triangle shape 1210, and the second bone piece has a second mating feature (e.g. a recess) having a circle shape 1220. In some cases, the radial overlap O may be about 0.016 inches. In some instances, other radial overlap distances O may be used. As shown here, triangle shape 1210 includes biting edges 1212 that more forcefully impinge against the circle shape 1220 of the second mating feature, whereas other portions (e.g. 1214) of the triangle shape do not so forcefully impinge upon the second mating feature, or in some locations (e.g. 1216) the triangle shape does not radially impinge against the second mating feature at all. Hence, as shown here, the biting edge 1212 can extend into the circle shape to the extent of the radial overlap O distance.

Figure 13:
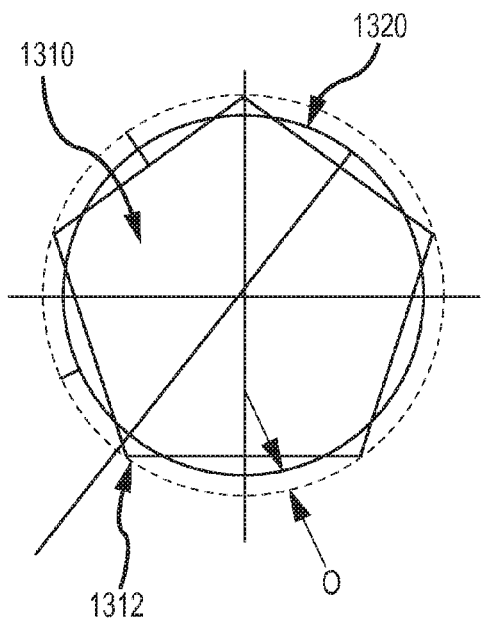
FIG. 13 depicts aspects of bone graft assemblies, their use, and/or manufacture, according to embodiments of the present invention.

FIG. 13 presents another related configuration, where the first bone piece has a first mating feature (e.g. a pin) with a pentagon shape 1310, and the second bone piece has a second mating feature (e.g. a recess) having a circle shape 1320. In some cases, the radial overlap may be about 0.005 inches. In some instances, other radial overlap distances O may be used. As shown here, pentagon shape 1310 includes biting edges that more forcefully impinge against the circle shape 1320 of the second mating feature, whereas other portions of the pentagon shape do not so forcefully impinge upon the second mating feature, or in some locations the pentagon shape does not radially impinge against the second mating feature at all. Hence, as shown here, the biting edge 1312 can extend into the circle shape to the extent of the radial overlap O distance.

Figure 14:
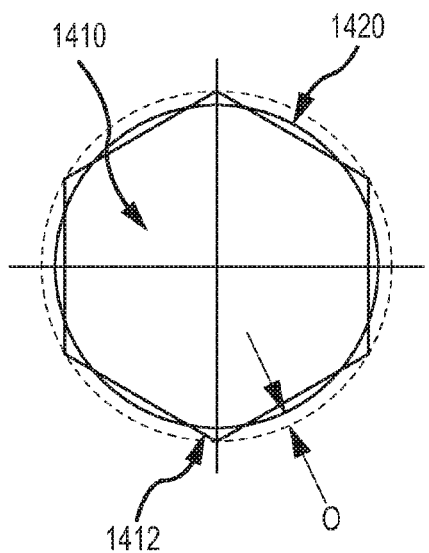
FIG. 14 depicts aspects of bone graft assemblies, their use, and/or manufacture, according to embodiments of the present invention.

FIG. 14 presents yet another related configuration, where the first bone piece has a first mating feature (e.g. pin) with a hexagon shape 1410, and the second bone piece has a second mating feature (e.g. recess) having a circle shape 1420. In some cases, the overlap may be about 0.003 inches. In some instances, other radial overlap distances O may be used. As shown here, hexagon shape 1410 includes biting edges that more forcefully impinge against the circle shape 1420 of the second mating feature, whereas other portions of the hexagon shape do not so forcefully impinge upon the second mating feature, or in some locations the hexagon shape does not radially impinge against the second mating feature at all. Hence, as shown here, the biting edge 1412 can extend into the circle shape to the extent of the radial overlap O distance.

Figure 15:
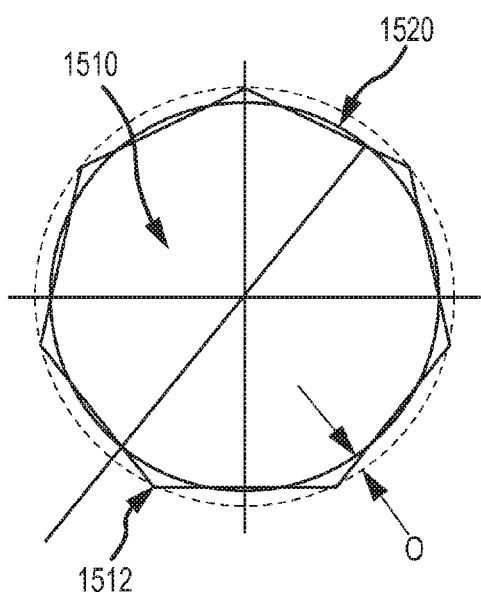
FIG. 15 depicts aspects of bone graft assemblies, their use, and/or manufacture, according to embodiments of the present invention.

FIG. 15 presents still a further related configuration, where the first bone piece has a first mating feature (e.g. pin) with a heptagon shape 1510, and the second bone piece has a second mating feature (e.g. recess) having a circle shape 1520. In some cases, the overlap may be about 0.002 inches. In some instances, other radial overlap distances O may be used. As shown here, heptagon shape 1510 includes biting edges that more forcefully impinge against the circle shape 1520 of the second mating feature, whereas other portions of the heptagon shape do not so forcefully impinge upon the second mating feature, or in some locations the heptagon shape does not radially impinge against the second mating feature at all. Hence, as shown here, the biting edge 1512 can extend into the circle shape to the extent of the radial overlap O distance.

Figure 16:
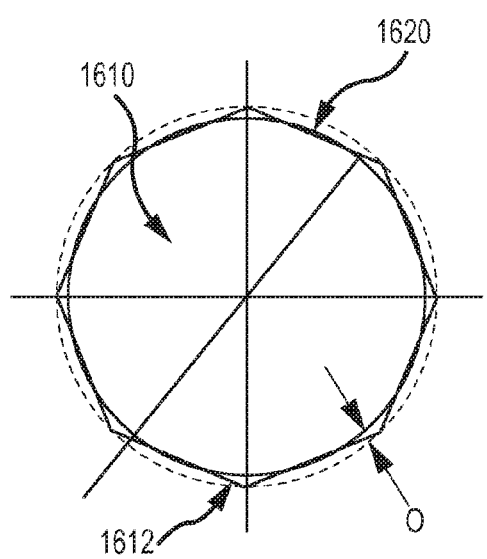
FIG. 16 depicts aspects of bone graft assemblies, their use, and/or manufacture, according to embodiments of the present invention.

FIG. 16 presents another related configuration, where the first bone piece has a first mating feature (e.g. pin) with an octagon shape 1610, and the second bone piece has a second mating feature (e.g. recess) having a circle shape 1620. In some cases, the overlap may be about 0.002 inches. In some instances, other radial overlap distances O may be used. As shown here, octagon shape 1610 includes biting edges that more forcefully impinge against the circle shape 1620 of the second mating feature, whereas other portions of the octagon shape do not so forcefully impinge upon the second mating feature, or in some locations the octagon shape does not radially impinge against the second mating feature at all. Hence, as shown here, the biting edge 1612 can extend into the circle shape to the extent of the radial overlap O distance.

Figure 17A:
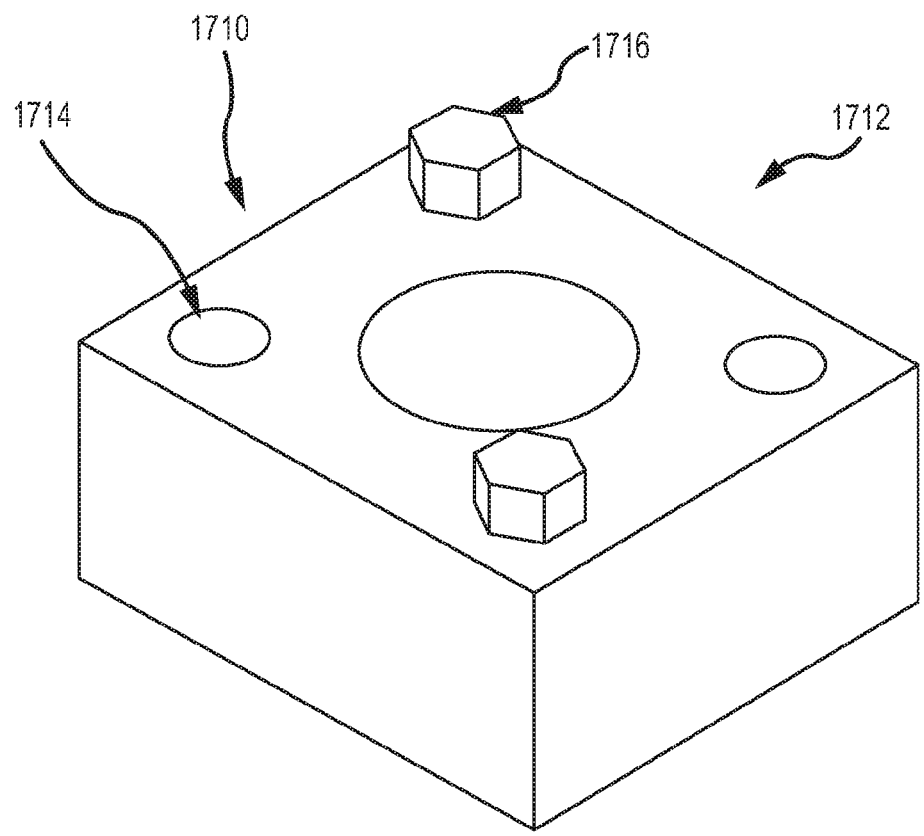
FIGS. 17A and 17B illustrate aspects of bone graft assemblies, their use, and/or manufacture, according to embodiments of the present invention.
Figure 17B:
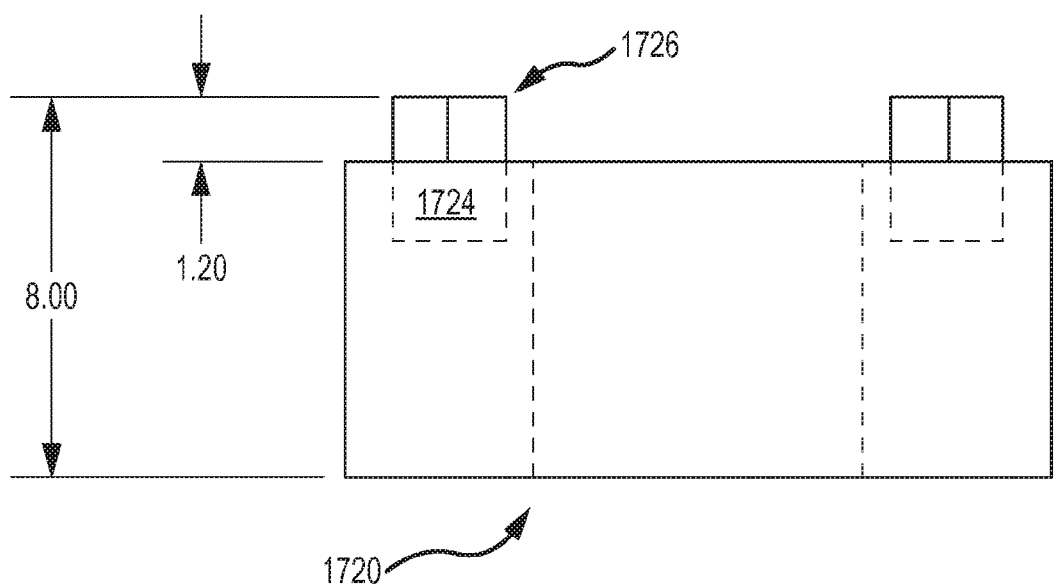

As shown in FIGS. 17A and 17B, a bone graft assembly 1700 can include a first bone piece 1710 having a first mating feature 1712 and a second bone piece 1720 having a second mating feature 1722. The first mating feature (e.g. two hex pins and two round pockets) has a shape that is non-complimentary to the shape of the second mating feature (e.g. two hex pins and two round pockets). When the first and second bone pieces are coupled or pressed together, an interface between the first and second mating features is defined by a non-uniform press fit. This configuration presents a universal design, wherein two bone pieces, each having the same shape, can be joined to form a bone graft assembly. When coupled, the mating features are hidden. According to some embodiments, the press fit is relatively easy to establish, although it may be very difficult to pull apart. The dimensions depicted here (in millimeters) may be varied or adjusted according to the use for which the assembly is intended. For example, the dimensions can be adjusted for appropriate use in a cervical spacer application, a vertebral spacer application, and the like. In some instances, assembly 900 may also include a pin or plug 930 (e.g. that includes cancellous bone material) that extends through corresponding apertures (940, 950) in the first and second bone pieces.

Hence, two graft pieces can be joined together by creating a round female on one piece and a corresponding hexagonal boss on the other piece. For example, as shown here, first piece include recess 1714 and boss 1716, and second piece includes boss 1726 and recess 1724. As depicted in FIG. 14, in some cases the hexagonal boss can be created with an interference fit where the mid-point between the circumscribed diameter and the inscribed diameter is the same size as the round hole. When the two graft pieces are pressed together, a non-uniform interference fit is formed. In some cases, a first graft piece includes one or more bosses, and a second graft piece includes one or more corresponding recesses. In some cases, as depicted in FIGS. 17A and 17B, the first graft piece can include a combination of bosses and recesses, and the second graft piece can include a corresponding combination of recesses and bosses. In this way, the configuration can present a universal blank or graft piece, where a single shape can function as both the first piece and the second piece. In addition to hexagonal boss shapes, graft pieces according to embodiments of the present invention may be configured to present any desired polygonal boss shape (e.g. as depicted in FIGS. 11-16).

Figure 18A:
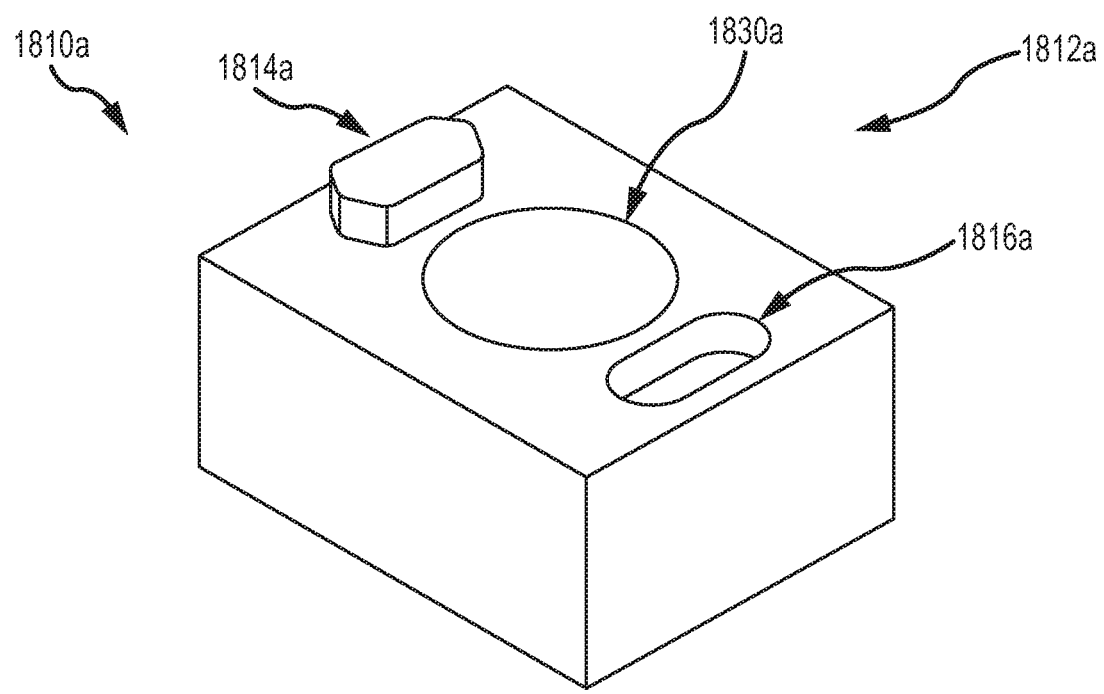
FIGS. 18A to 18D illustrate aspects of bone graft assemblies, their use, and/or manufacture, according to embodiments of the present invention.
Figure 18B:
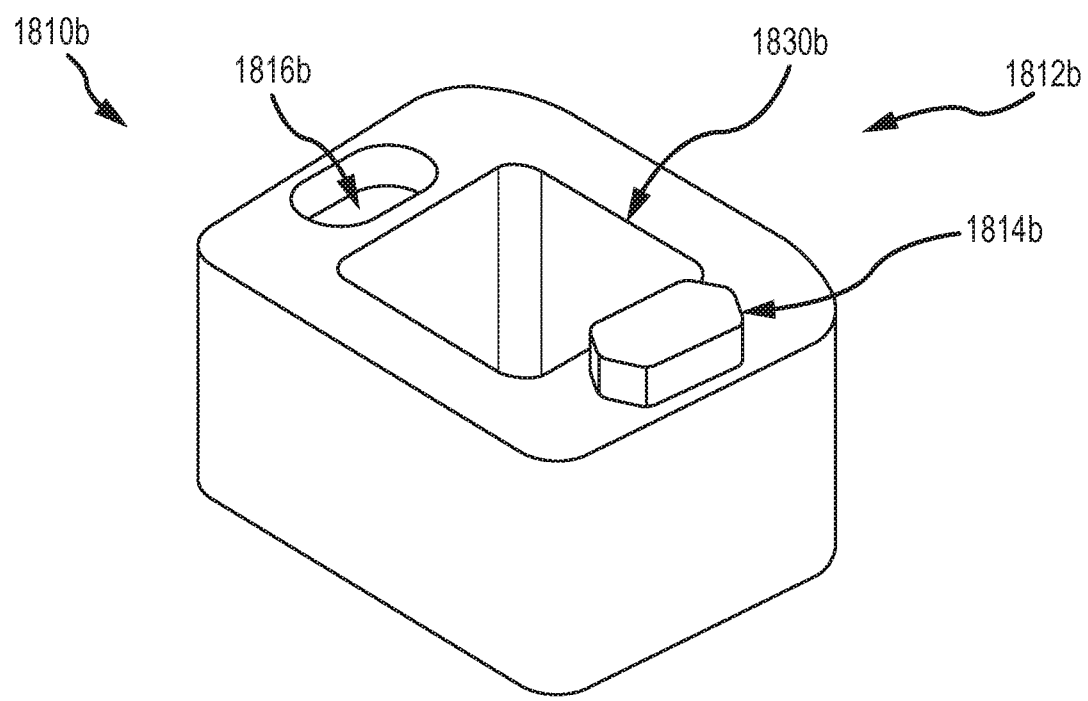

FIGS. 18A and 18B illustrate another bone graft assembly configurations according to embodiments of the present invention. A bone graft assembly can include a first bone piece 1810a having a first mating feature 1812a and a second bone piece (not shown, but can be similar or identical to first bone piece) having a second mating feature. As shown here, bone piece 1810a also includes an aperture or chamber 1830a. The first mating feature (e.g. irregular hex pin 1814a and race track or canal pocket 1816a) has a shape that is non-complimentary to the shape of the second mating feature (e.g. corresponding irregular hex pin and race track or canal pocket). When the first and second bone pieces are coupled or pressed together, an interface between the first and second mating features is defined by a non-uniform press fit. A racetrack shape can be presented as a rectangle with semi-circular rounded ends. In addition to the hex pin 1814a shown here, embodiments may optionally present any of a variety of other polygonal pin shapes shape (e.g. as depicted in FIGS. 11-16).

As depicted in FIG. 18B, a bone graft assembly can include a first bone piece 1810b having a first mating feature 1812b and a second bone piece (not shown, but can be similar or identical to first bone piece) having a second mating feature. The first mating feature (e.g. irregular hex pin 1814b and race track or canal pocket 1816b) has a shape that is non-complimentary to the shape of the second mating feature (e.g. irregular hex pin and race track or canal pocket). When the first and second bone pieces are coupled or pressed together, an interface between the first and second mating features is defined by a non-uniform press fit. A racetrack shape can be presented as a rectangle with semi-circular rounded ends. In addition to the hex pin 1814b shown here, embodiments may optionally present any of a variety of other polygonal pin shapes. The bone piece of FIG. 18B has rounded edges, as compared to the bone piece of FIG. 18A which has square edges.

Hence, as shown here, two graft pieces can be joined together in such a way that an elongated hexagonal boss of a first piece is pressed into an oval shaped canal of a second piece. In some cases, the first graft piece can include a combination elongated hexagonal boss and oval shaped canal, and the second graft piece can include a corresponding combination oval shaped canal and elongated hexagonal boss. In this way, the configuration can present a universal blank or graft piece, where a single shape can function as both the first piece and the second piece. As shown in FIG. 18A, the pin mating feature is centrally positioned on the graft piece.

Figure 18C:
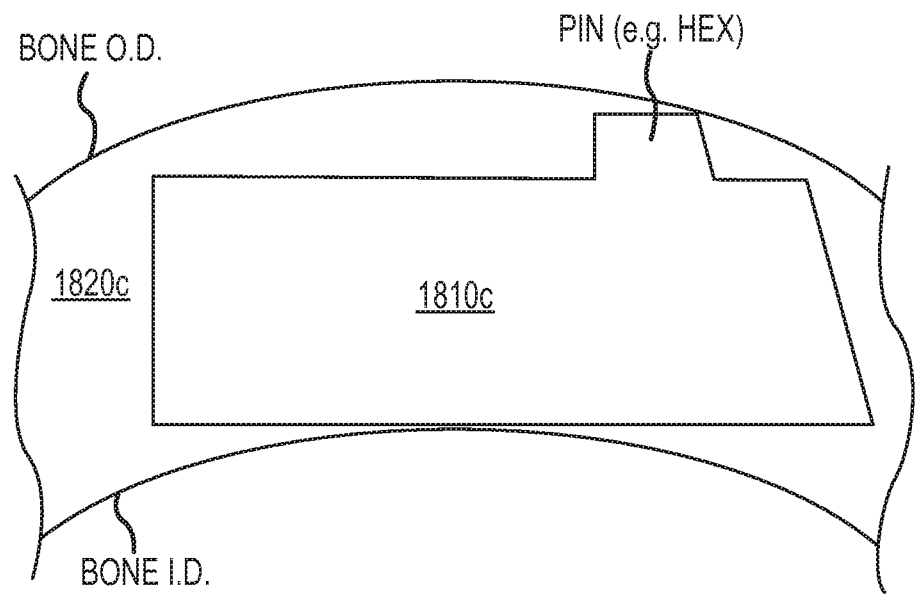
Figure 18D:
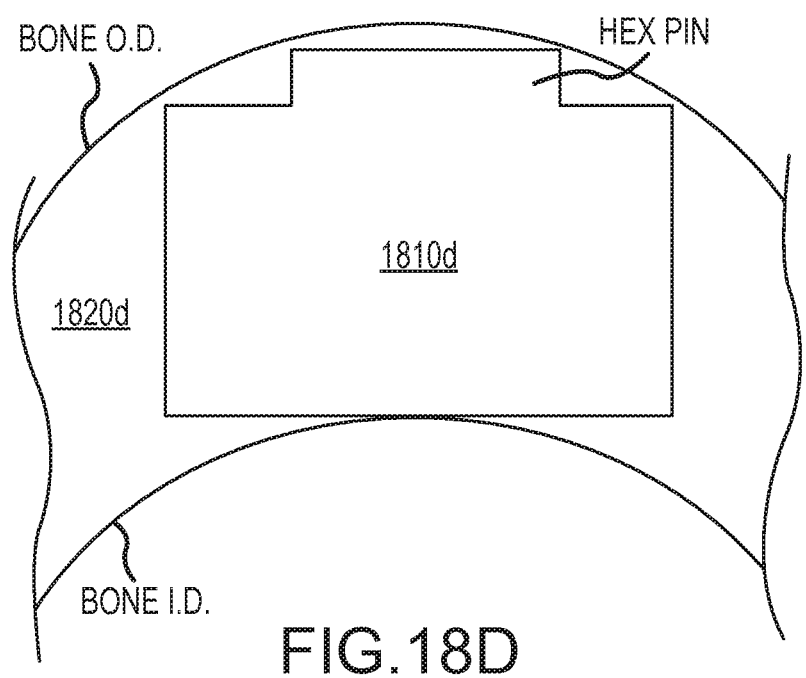

FIGS. 18C and 18D illustrate how bone pieces (1810c, 1810d) may be obtained from donor bone graft sites. For example, the bone pieces can be obtained from a tubular donor bone constructs (1820c, 1820d) having an inner diameter (I.D.) and an outer diameter (O.D.).

Cleaning and Freeze Drying

Bone graft pieces were soaked in 3% peroxide for approximately 5 hrs, which resulted in normal cleaning effects on the color of the tissue and no visual effects on the mating feature. Grafts were individually packaged in 4×6 Tyvek and freeze dried. It was observed that the mating features tolerated the freeze drying process well, with no noticeable side effects (e.g. cracking by expansion or separation from shrinkage).

Pull Testing for Pocket and Hex Pin Configurations

Figures 19, 20:
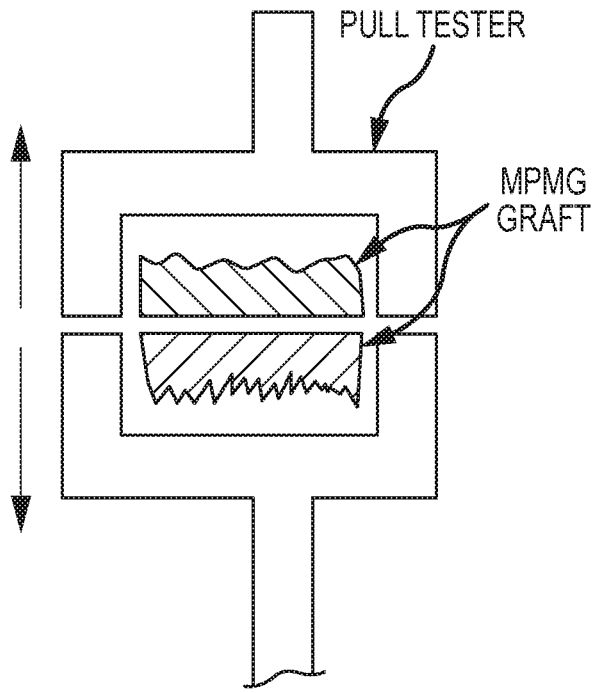
FIG. 19 depicts aspects of bone graft assemblies, their use, and/or manufacture, according to embodiments of the present invention.
FIG. 20 depicts aspects of bone graft assemblies, their use, and/or manufacture, according to embodiments of the present invention.

Pull testing was performed on 3 samples of each configuration, using a TT003 apparatus similar to that illustrated in FIG. 19. The pocket configuration was similar to that illustrated in FIG. 5A, and the hex pin configuration was similar to that illustrated in FIG. 17A. The results are shown in FIG. 20.

Additional Pocket Designs, with Window for Cancellous

Figure 21:
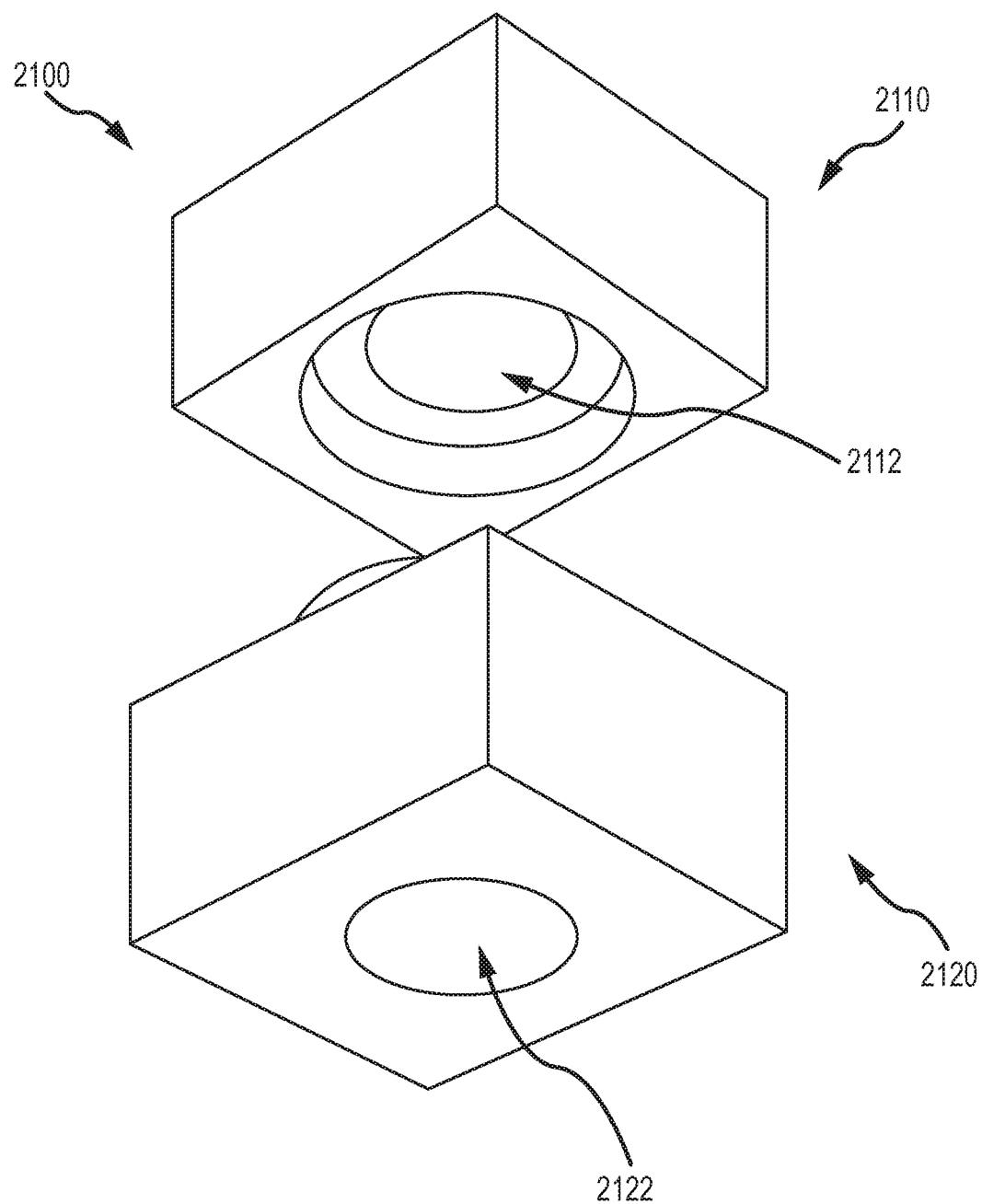
FIG. 21 depicts aspects of bone graft assemblies, their use, and/or manufacture, according to embodiments of the present invention.

FIG. 21 illustrates an exemplary multi-piece bone graft assembly 2100 according to embodiments of the present invention. Assembly 2100 includes a first cortical bone piece 2110 having a first mating feature or boss, and a second cortical bone piece 2120 having a second mating feature or pocket. Optionally, a cancellous pin or plug that can be inserted through both the first and second cortical bone pieces (e.g. via apertures 2112 and 2122). As shown here, the first and second bone pieces engage in such a way that the mating features are enclosed or hidden from view when the bone pieces are combined. This configuration provides a large amount of surface area for mating. Further, the pieces can be constructed without removing a significant amount of graft material. In some cases, the bone pieces can be constructed with a line to line tolerance.

Figure 22:
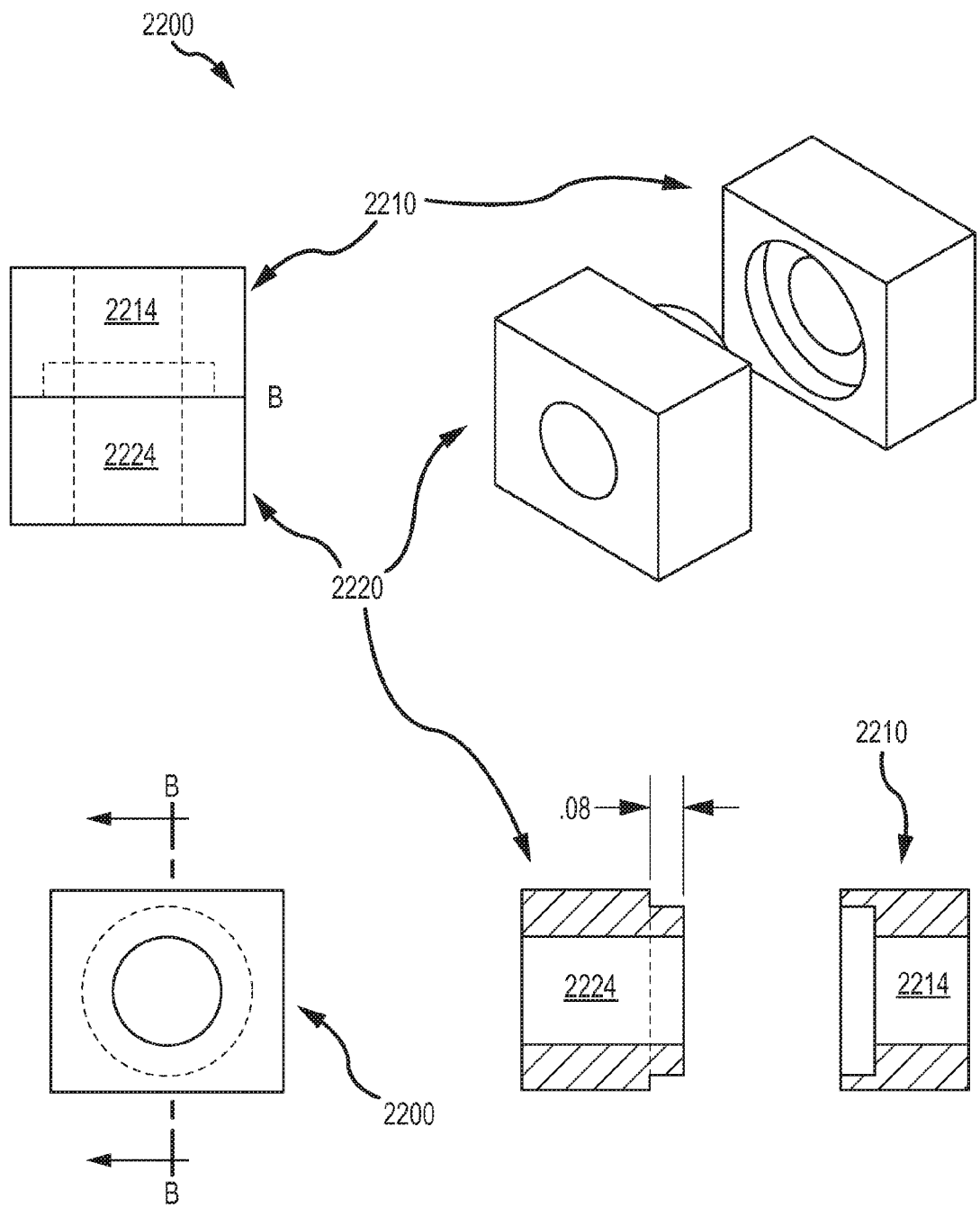
FIG. 22 depicts aspects of bone graft assemblies, their use, and/or manufacture, according to embodiments of the present invention.

FIG. 22 illustrates an exemplary multi-piece bone graft assembly 2200 according to embodiments of the present invention. Assembly 2200 includes a first cortical bone piece 2210 having a first mating feature or boss, and a second cortical bone piece 2220 having a second mating feature or pocket. Optionally, a cancellous pin or plug that can be inserted through both the first and second cortical bone pieces (e.g. via apertures 2214 and 2224). As shown here, the first and second bone pieces engage in such a way that the mating features are enclosed or hidden from view when the bone pieces are combined. This configuration provides a large amount of surface area for mating. Further, the pieces can be constructed without removing a significant amount of graft material. In some cases, the bone pieces can be constructed with a line to line tolerance.

Figure 23:
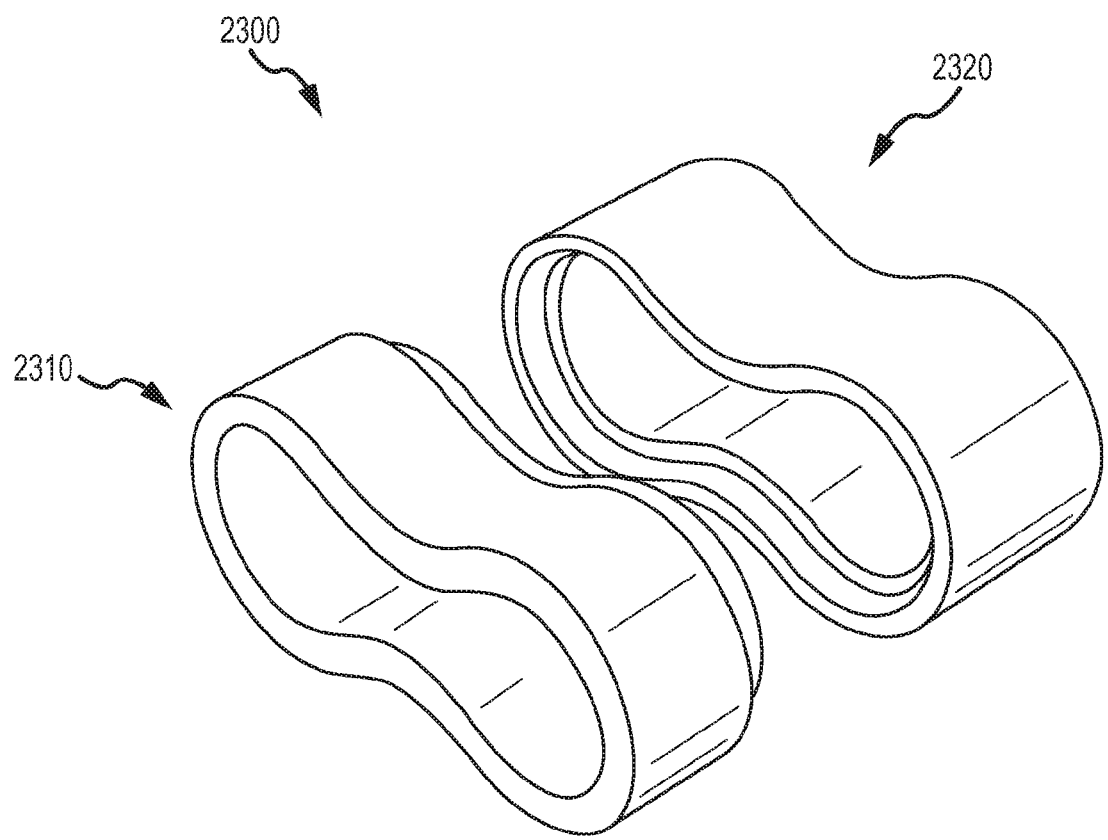
FIG. 23 depicts aspects of bone graft assemblies, their use, and/or manufacture, according to embodiments of the present invention.

FIG. 23 illustrates an exemplary multi-piece bone graft assembly 2300 according to embodiments of the present invention. Assembly 2300 includes a first cortical bone piece 2310 having a first mating feature or boss, and a second cortical bone piece 2320 having a second mating feature or pocket.

Figure 24:
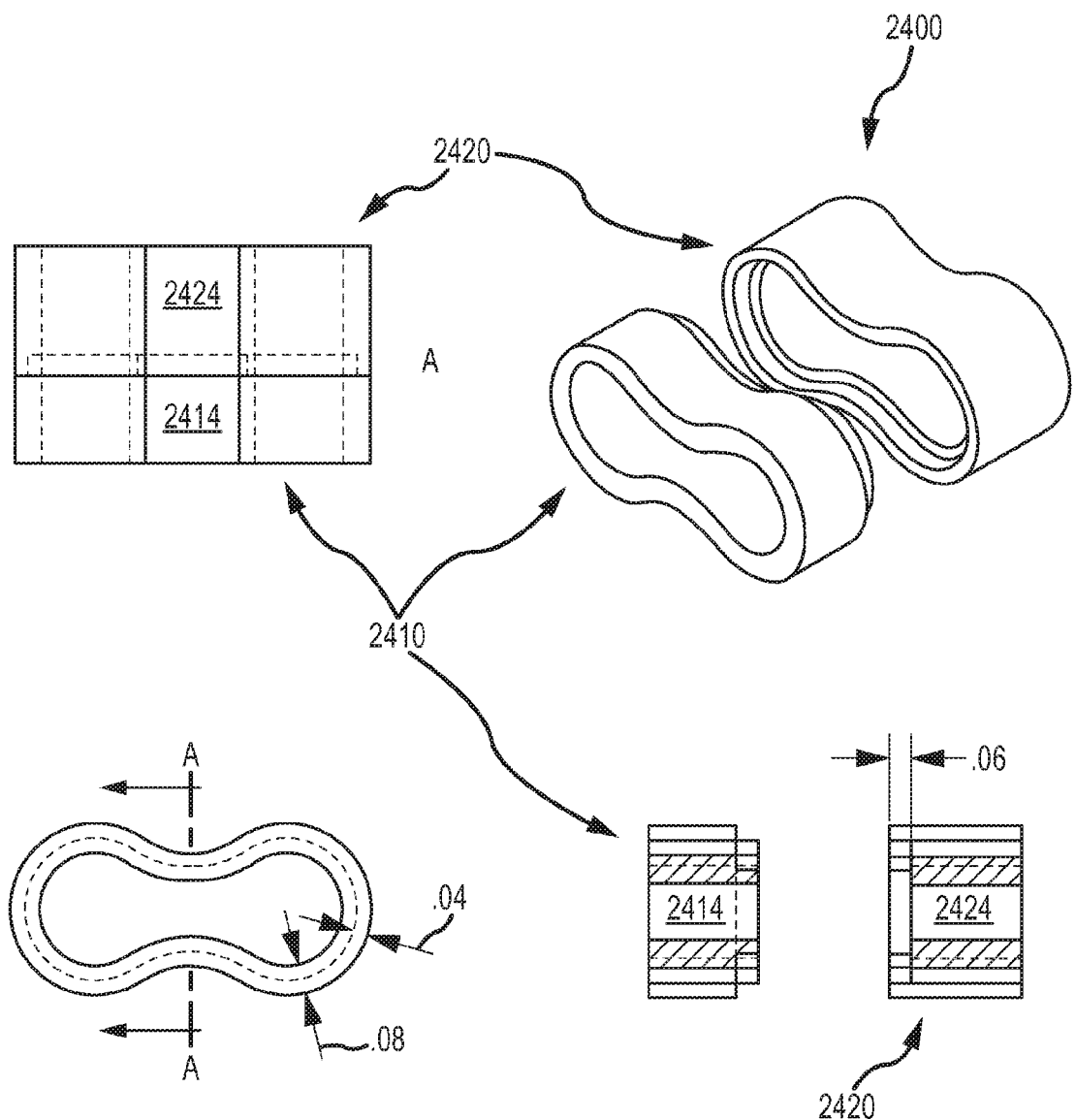
FIG. 24 depicts aspects of bone graft assemblies, their use, and/or manufacture, according to embodiments of the present invention.

FIG. 24 illustrates an exemplary multi-piece bone graft assembly 2400 according to embodiments of the present invention. Assembly 2400 includes a first cortical bone piece having a first mating feature or boss, and a second cortical bone piece having a second mating feature or pocket. Assembly 2400 includes a first cortical bone piece 2410 having a first mating feature or boss, and a second cortical bone piece 2420 having a second mating feature or pocket. Optionally, a cancellous pin or plug that can be inserted through both the first and second cortical bone pieces (e.g. via apertures 2414 and 2424). As shown here, the first and second bone pieces engage in such a way that the mating features are enclosed or hidden from view when the bone pieces are combined. This configuration provides a large amount of surface area for mating. Further, the pieces can be constructed without removing a significant amount of graft material. In some cases, the bone pieces can be constructed with a line to line tolerance.

Figure 25:
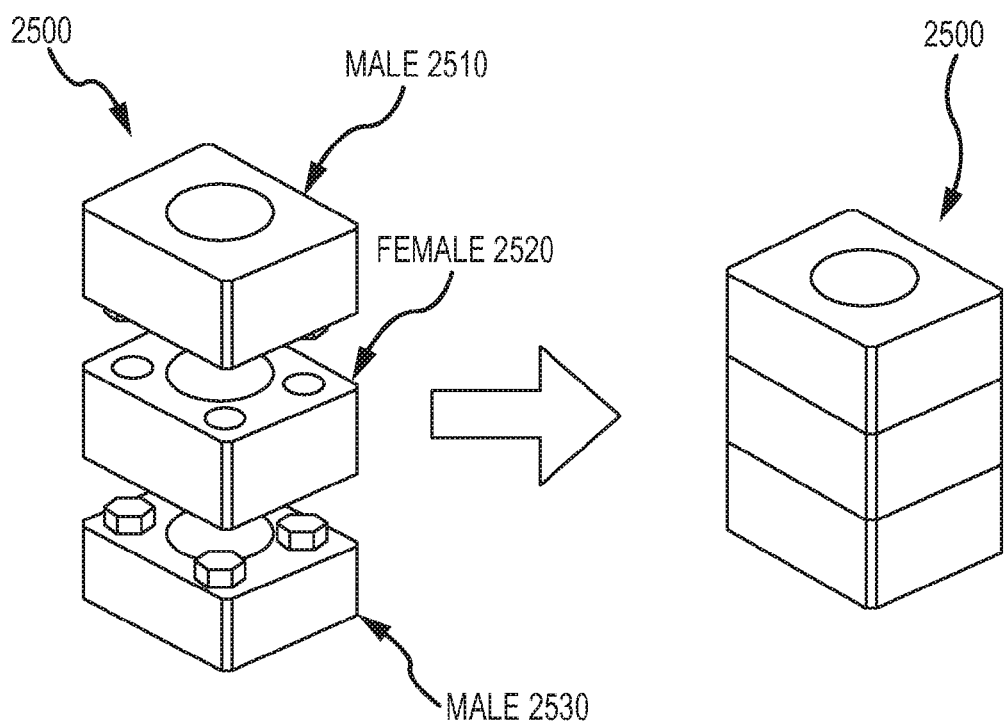
FIG. 25 depicts aspects of bone graft assemblies, their use, and/or manufacture, according to embodiments of the present invention.
Figure 25:
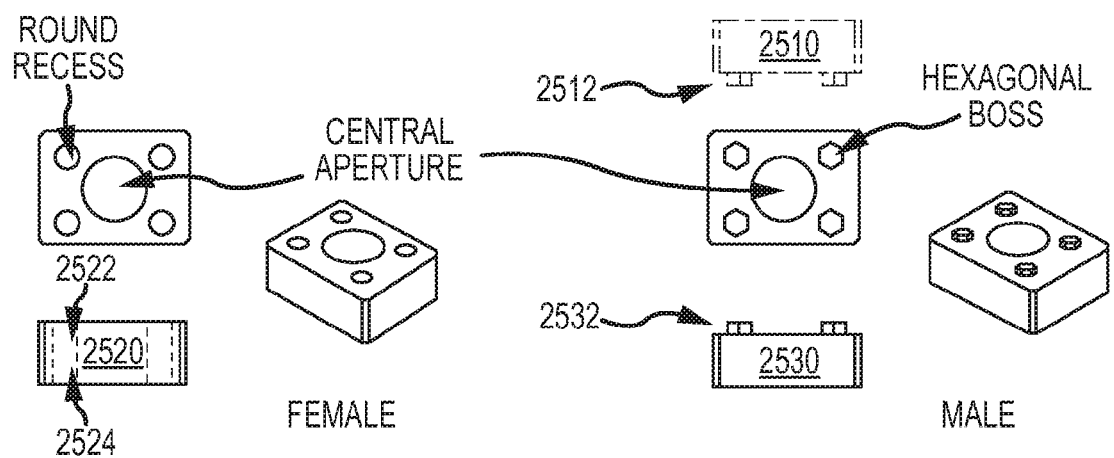

FIG. 25 illustrates an exemplary multi-piece bone graft assembly 2500 according to embodiments of the present invention. Assembly 2500 includes a first bone piece 2510 having a mating feature 2512, a second bone piece 2520 having mating features 2522, 2524, and a third bone piece 2530 having a mating feature 2532. Here, mating feature 2512 has a shape (e.g. hexagonal boss) that is non-complimentary to a shape (e.g. round recess) of mating feature 2522. Similarly, mating feature 2532 has a shape (e.g. hexagonal boss) that is non-complimentary to a shape (e.g. round recess) of mating feature 2524. When first and second bone pieces 2510, 2520, are coupled, an interface between mating features 2512, 2522 is defined by a non-uniform press fit. Similarly, when second and third bone pieces 2520, 2530 are coupled, an interface between mating features 2522, 2532 is defined by a non-uniform press fit. As shown here, bone graft assembly 2500 includes three stacked bone pieces. It is understood, however, that by fabricating multiple bone pieces having appropriate mating features, embodiments of the present invention encompass bone graft assemblies having any desired number of stackable pieces.

Figure 26:
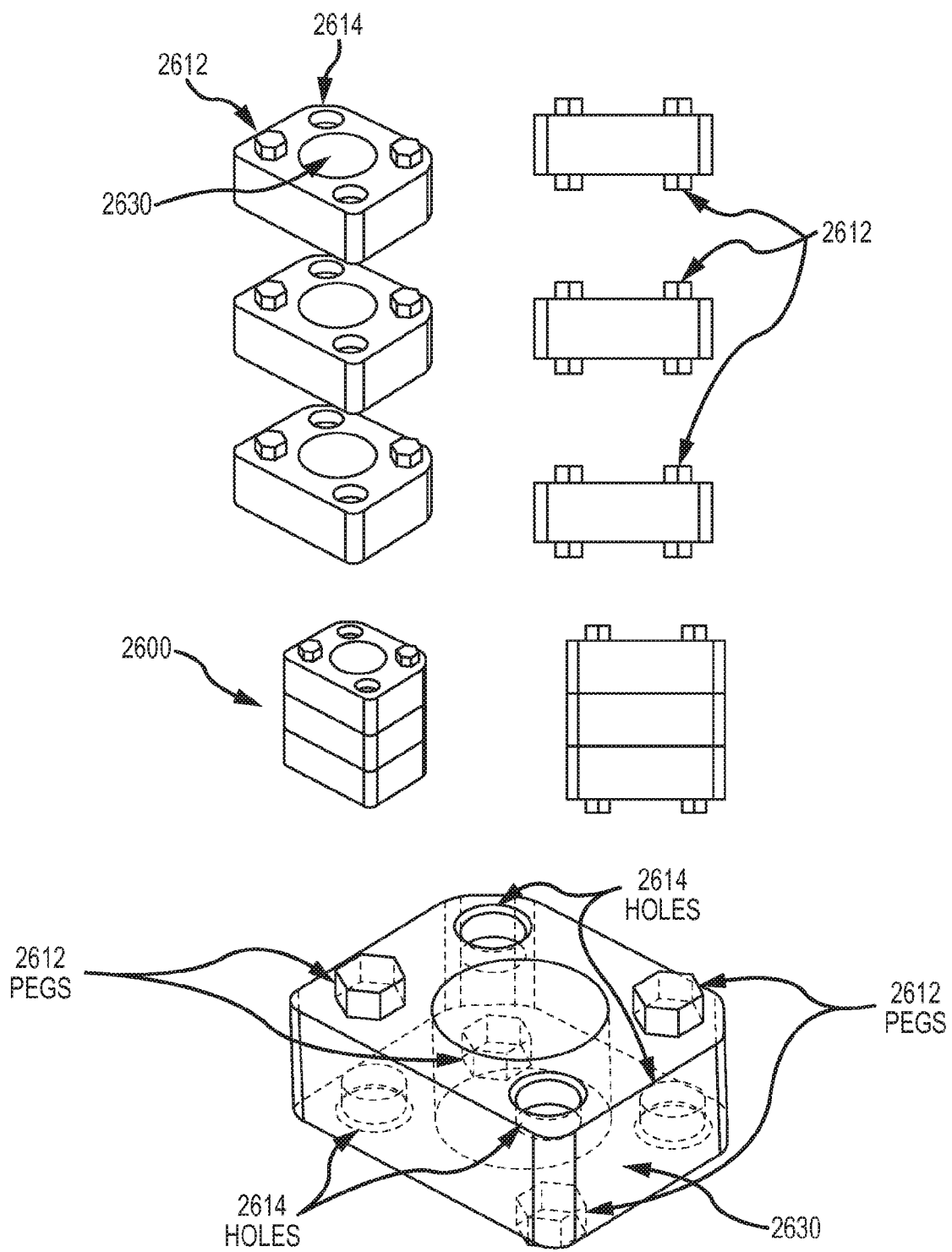
FIGS. 26 and 26A show aspects of bone graft assemblies, their use, and/or manufacture, according to embodiments of the present invention.

FIG. 26 illustrates another exemplary multi-piece bone graft assembly 2600 according to embodiments of the present invention. The assembly includes multiple bone pieces 2610, each with one or more mating features. Respective mating features of different bone pieces have non-complimentary shapes, so that multiple pieces can be coupled together in a stacked arrangement, and interfaces between adjacent bone pieces can be defined by non-uniform press fits. For example, bone piece 2610 may include pegs or bosses 2612 having a hexagonal configuration and recesses or holes 2614 having circular configurations. As shown here, a bone piece 2610 may include an aperture or passage 2630.

Figure 26A:
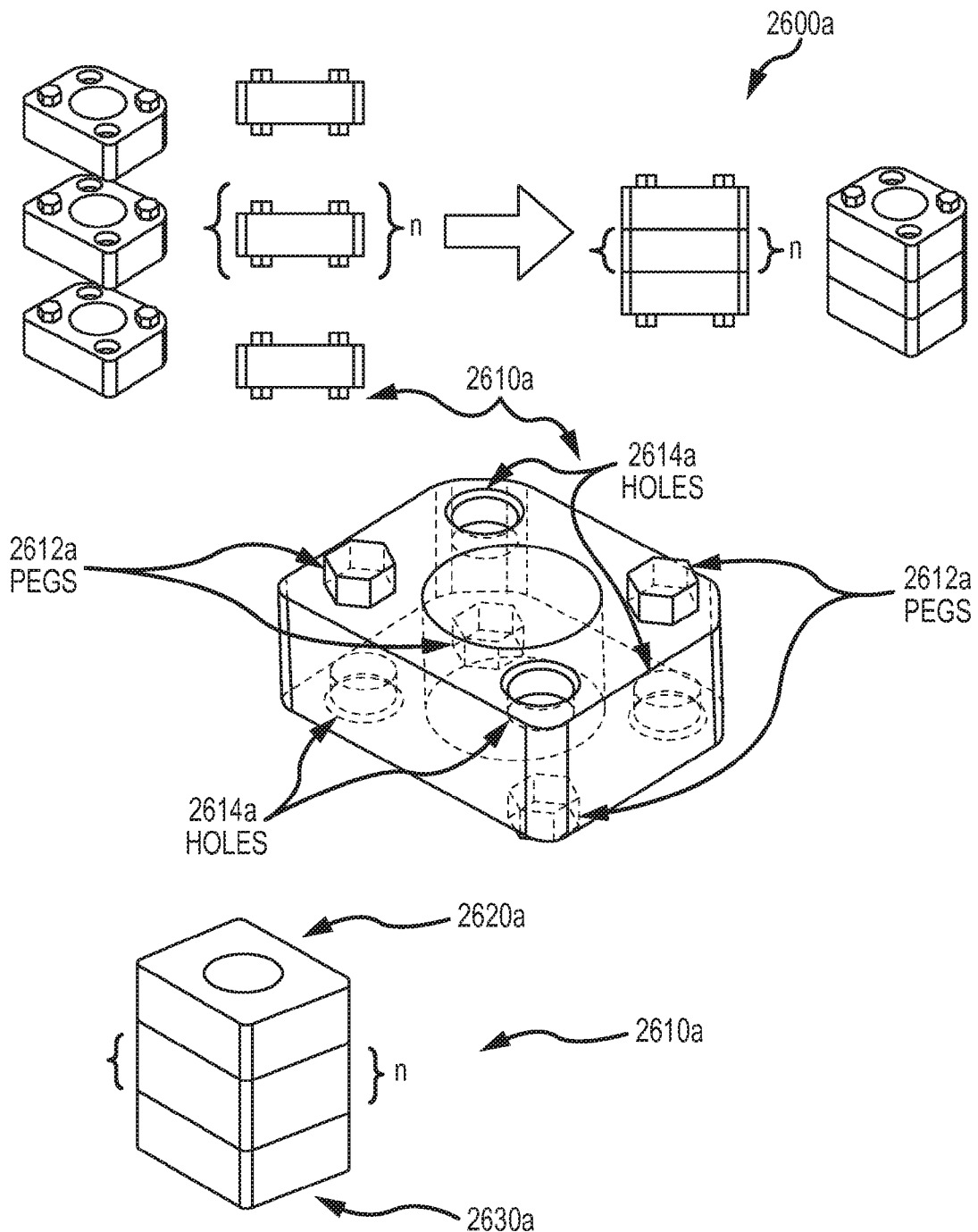

FIG. 26A illustrates another exemplary multi-piece bone graft assembly 2600a according to embodiments of the present invention. The assembly includes multiple bone pieces, each with a mating feature. Respective mating features of bone pieces 2610a have non-complimentary shapes (e.g. hexagonal peg 2612a, round hole 2614a) so that individual pieces can be coupled together in a stacked arrangement and interfaces between adjacent bone pieces can be defined by non-uniform press fits. As shown here, the graft assembly can include any number of pieces or layers (e.g. 2+n) as desired, where n is any integer. As such, the graft assembly can be considered to include an intermediate or auxiliary bone piece construct having n pieces. In some instances, the end pieces may present a flat surface or otherwise be void of any protruberances, as depicted by the end pieces 2620a and 2630a of assembly 2610a.

Figure 27:
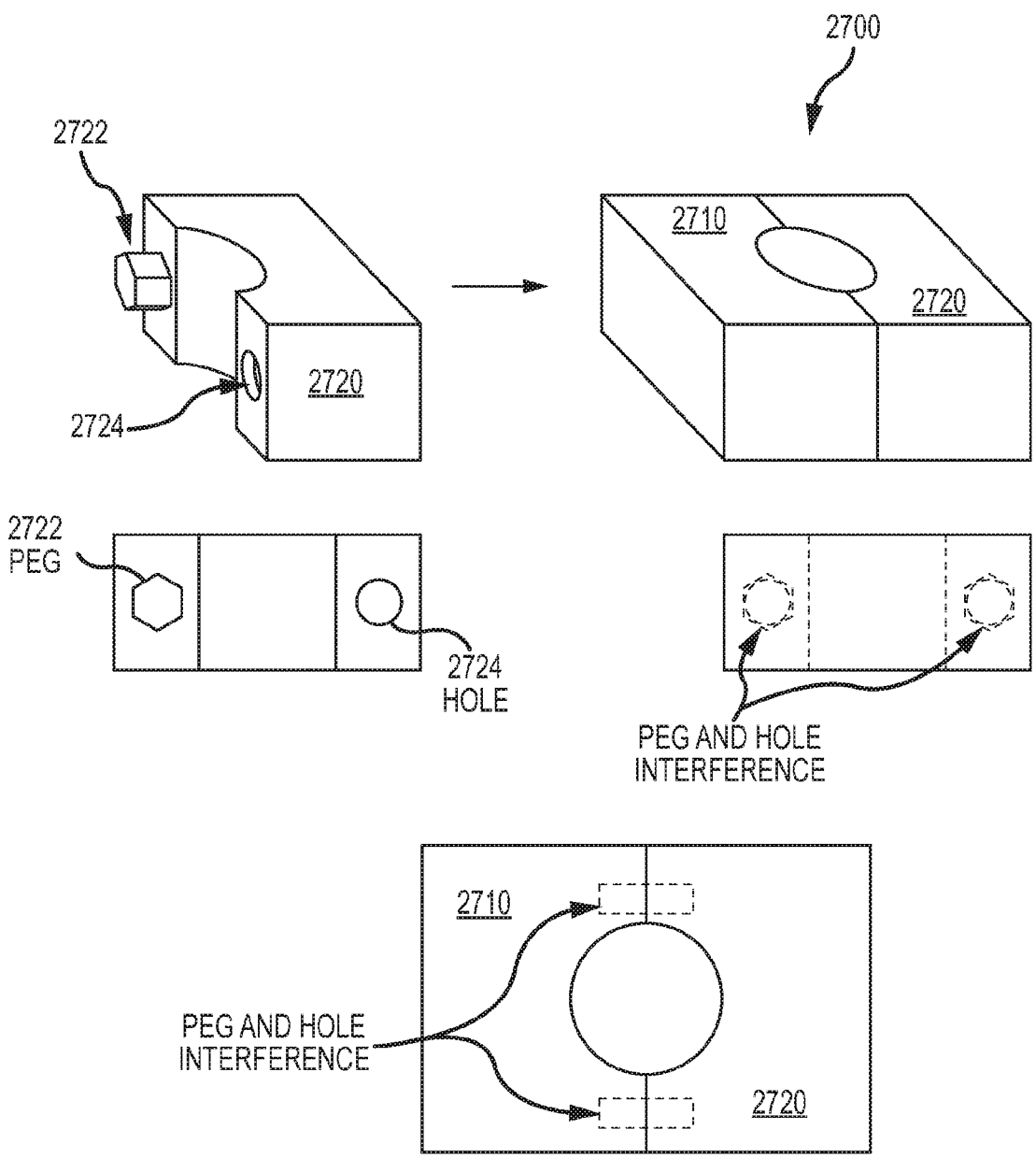
FIG. 27 depicts aspects of bone graft assemblies, their use, and/or manufacture, according to embodiments of the present invention.

FIG. 27 illustrates another exemplary multi-piece bone graft assembly 2700 according to embodiments of the present invention. The assembly includes multiple bone pieces (e.g. 2710, 2720), each with a mating feature. Respective mating features of bone pieces have non-complimentary shapes, so that individual pieces can be coupled together in a stacked arrangement (either vertically, horizontally, or both vertically and horizontally), and interfaces between adjacent bone pieces can be defined by non-uniform press fits. For example, bone piece 2720 may include a mating feature having a hexagonal peg 2722 and a round hole 2724. As shown there, the mating between two pieces is provide laterally (side to side), as compared with the top-bottom stacking arrangements of FIGS. 25 and 26, for example.

Figure 28:
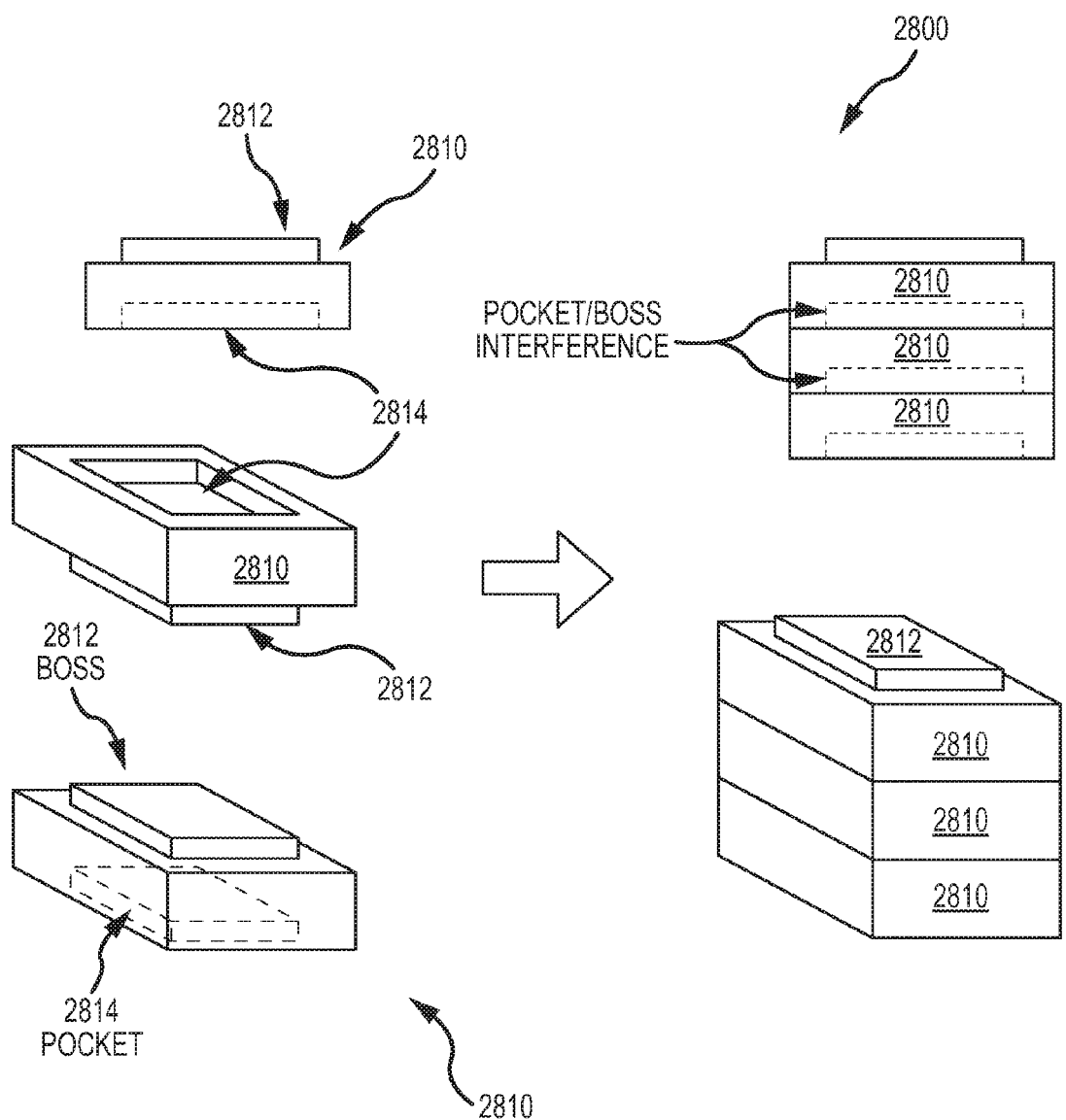
FIG. 28 depicts aspects of bone graft assemblies, their use, and/or manufacture, according to embodiments of the present invention.

FIG. 28 illustrates another exemplary multi-piece bone graft assembly 2800 according to embodiments of the present invention. The assembly includes multiple bone pieces, each with a mating feature. Respective mating features of bone pieces have non-complimentary shapes, so that individual pieces can be coupled together in a stacked arrangement (either vertically, horizontally, or both vertically and horizontally), and interfaces between adjacent bone pieces can be defined by non-uniform press fits. For example, bone piece 2810 includes a raised boss 2812 on one side of the piece, and a recessed pocket 2814 on an opposing side of the piece. As shown here, respective mating features of individual pieces can be configured to provide, when approximated, a hidden engagement zone as describe elsewhere herein.

Figure 29:
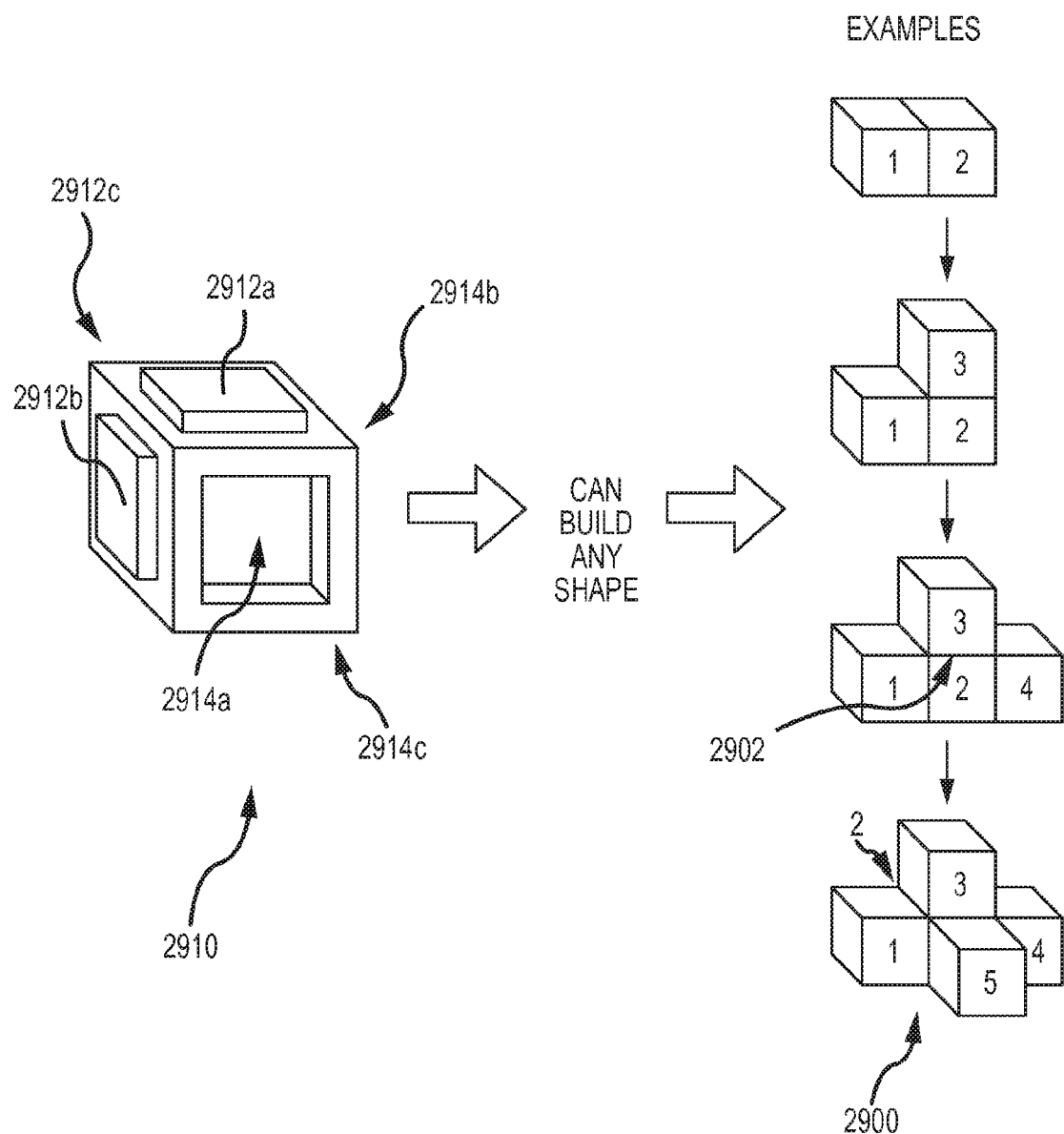
FIG. 29 depicts aspects of bone graft assemblies, their use, and/or manufacture, according to embodiments of the present invention.

FIG. 29 illustrates another exemplary multi-piece bone graft assembly 2900 according to embodiments of the present invention. The assembly includes multiple bone pieces, and individual bone pieces have one or more mating features. Respective mating features of bone pieces have non-complimentary shapes, so that individual pieces can be coupled together in a stacked arrangement (either vertically, horizontally, or both vertically and horizontally), and interfaces between adjacent bone pieces can be defined by non-uniform press fits. As shown here, respective mating features of individual pieces can be configured to provide, when approximated, a hidden engagement zone 2902 as describe elsewhere herein. Using such a buildable and stackable design, it is possible to create any size and shape of a graft assembly, having any number of graft pieces. As depicted here, a graft piece may have six sides, each with a mating feature (e.g. three male mating features and three female mating features). For example, bone piece 2910 includes bosses 2912a, 2912b, and 2912c, as well as pockets 2914a, 2914b, and 2914c. In related instances, a bone piece may have four sides, five sides, seven sides, or any other desired number of sides. The boss and pocket mating features shown in this configuration may also be provided as hexagonal boss and round recess interfaces, or as any of the other mating feature designs as disclosed herein. As shown here, the bone graft assembly includes an intermediate or auxiliary bone piece construct (e.g. pieces 2, 3, and 5). The intermediate bone piece construct can include a bone piece pair (e.g. pieces 2 and 3) having a first bone piece (e.g. piece 2) with a first mating feature and a second bone piece (e.g. piece 3) with a second mating feature. The first mating feature of first bone piece of the bone piece pair and the second mating feature of the second bone piece of the bone piece pair can be configured to provide, when approximated, a bone piece pair hidden engagement zone.

An exemplary procedure may involve creating a tissue blank using custom tooling and a small flat end mill on a CNC (computer numerically controlled) machine, where the overall shape of the graft (ID and OD) and the mating features are milled at the same time with one tool path/operation. The mating feature geometry can be designed taking into consideration the size and functionality of the end mill and the CNC. For example, a round endmill can be used to create a round hole. A bone blank can be milled out of a larger segment of bone that has previously been examined and supplied. After the graft piece has been cut, it may naturally fall out of the larger section of bone, or it may be removed by any other means desired, without damaging the mating features. After a multiple number of the individual graft pieces are created, they can be pressed together, for example manually or by using a vise, to insure a full and complete press while maintaining the proper alignment. In some cases, such assembled grafts can be placed into other vise fixtures for further processing or to complete the manufacturing of the graft.

In some instances, individual graft pieces can be milled out of human donated bone, which may be for example femoral and tibial shafts. Techniques may include using a CNC with a small end mill to mill out these parts. In this way, it is possible to create a very precise profile and hold tight tolerances while manufacturing the mating features. The operator can place the material in a vise and program or instruct the machine where to start milling. During the milling session it is possible to program the toolpaths to run at curtain feed rates and spindle speeds to control the precision of the graft mating features. After a toolpath is complete, the tissue blank can be removed from the vise and the remaining shaft of the bone. During assembly, it is possible to another vise to press multiple graft pieces together. Many multi-piece graft assemblies involve a male boss and female recess press fit. In some instances, a finish surface on a bone can be within a range between 16G to 500M finish. Embodiments encompass any of a variety of press fits and press fit classifications. For example, graft assemblies can be constructed to provide a press fit of FN1 or a LT1 per ANSI standard ANSI B4.1-1967 (R1999), incorporated herein by reference. Exemplary press fits can provide a coupling or fixation between components of a graft assembly, such that after the components are pressed together, friction prevents or inhibits them from coming apart or separating. The friction may be enhanced by compressive forces present between the coupled components.

Each of the operations described herein may be performed using a computer or other processor having hardware, software, and/or firmware, optionally in combination with a CNC or similar bone processing apparatus. Hence, CNC or other bone processing devices can be programmed to create the bone graft assembly components as disclosed herein. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patents, patent publications, patent applications, journal articles, books, technical references, and the like discussed in the instant disclosure are incorporated herein by reference in their entirety for all purposes.

It is to be understood that the figures and descriptions of the invention have been simplified to illustrate elements that are relevant for a clear understanding of the invention. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed is:

1. A bone graft assembly, comprising:
    a first bone piece having a first mating feature, the first mating feature comprising a peripheral surface, a medial surface, an inner surface, and a core surface; and
    a second bone piece having a second mating feature, the second mating feature comprising an outer surface, a peripheral surface, a medial surface, and an inner surface,
    wherein the first and second mating features are configured to provide, when approximated, a peripheral engagement zone defined between at least portions of the peripheral surfaces of the first and second mating features, respectively, a medial engagement zone defined between at least portions of the medial surfaces of the first and second mating features, respectively, and an inner engagement zone defined between at least portions of the inner surfaces of the first and second mating features, respectively,
    wherein the inner engagement zone is disposed interior to the medial engagement zone and the medial engagement zone is disposed interior to the peripheral engagement zone,
    wherein the medial engagement zone defines an interface having a first contour shape,
    wherein the core surface of the first mating feature defines an interface having a second contour shape,
    wherein the first contour shape is different from the second contour shape, and
    wherein the first contour shape is a rounded square and the second contour shape is a circle.

2. The bone graft assembly according to claim 1, wherein the first bone piece comprises a first bone piece aperture and the second bone piece comprises a second bone piece aperture, such that the first and second bone pieces are configured to provide, when approximated, a continuous aperture that extends through the first and second bone pieces of the bone graft assembly.

3. A bone graft assembly, comprising:
    a first bone piece having a first mating feature, the first mating feature comprising a peripheral surface, a medial surface, an inner surface, and a core surface; and
    a second bone piece having a second mating feature, the second mating feature comprising an outer surface, a peripheral surface, a medial surface, and an inner surface,
    wherein the first and second mating features are configured to provide, when approximated, a peripheral engagement zone defined between at least portions of the peripheral surfaces of the first and second mating features, respectively, a medial engagement zone defined between at least portions of the medial surfaces of the first and second mating features, respectively, and an inner engagement zone defined between at least portions of the inner surfaces of the first and second mating features, respectively, wherein the inner engagement zone is disposed interior to the medial engagement zone and the medial engagement zone is disposed interior to the peripheral engagement zone, wherein the medial engagement zone defines an interface having a first contour shape, wherein the core surface of the first mating feature defines an interface having a second contour shape, wherein the first contour shape is different from the second contour shape, wherein the first bone piece comprises a first bone piece aperture and the second bone piece comprises a second bone piece aperture, such that the first and second bone pieces are configured to provide, when approximated, a continuous aperture that extends through the first and second bone pieces of the bone graft assembly, and wherein the first bone piece aperture is defined by a circular circumference and the second bone piece aperture is defined by a circular circumference.

4. The bone graft assembly according to claim 2, wherein the continuous aperture is at least partially defined by the first and second mating features.

5. The bone graft assembly according to claim 2, further comprising a plug configured to extend through the corresponding apertures of the first and second bone pieces.

6. The bone graft assembly according to claim 5, wherein the plug comprises human cadaver donor bone material.

7. The bone graft assembly according to claim 6, wherein the human cadaver donor bone material of the plug comprises cancellous bone material.

8. The bone graft assembly according to claim 1, wherein the first bone piece comprises human cadaver donor bone material.

9. The bone graft assembly according to claim 8, wherein the human cadaver donor bone material of the first bone piece comprises cortical bone material.

10. The bone graft assembly according to claim 1, wherein the second bone piece comprises human cadaver donor bone material.

11. The bone graft assembly according to claim 10, wherein the human cadaver donor bone material of the second bone piece comprises cortical bone material.

12. The bone graft assembly according to claim 2, wherein the first bone piece core surface has a first bone piece core surface diameter, wherein the second bone piece core surface has a second bone piece core surface diameter, wherein the first bone piece aperture has a first bone piece aperture diameter, wherein the second bone piece aperture has a second bone piece aperture diameter, and wherein the first bone piece aperture diameter and the second bone piece aperture diameter are both greater than each of the first bone piece core surface diameter and the second bone piece core surface diameter.

13. The bone graft assembly according to claim 2, wherein the first bone piece aperture is defined by a circular circumference and the second bone piece aperture is defined by a circular circumference.

14. The bone graft assembly according to claim 1, wherein first and second contour shapes are concentric when the first and second mating features are approximated.

15. The bone graft assembly according to claim 3, wherein the continuous aperture is at least partially defined by the first and second mating features.

16. The bone graft assembly according to claim 3, further comprising a plug configured to extend through the corresponding apertures of the first and second bone pieces.

17. The bone graft assembly according to claim 16, wherein the plug comprises human cadaver donor bone material.

18. The bone graft assembly according to claim 17, wherein the human cadaver donor bone material of the plug comprises cancellous bone material.

19. The bone graft assembly according to claim 3, wherein the first bone piece comprises human cadaver donor bone material.

20. The bone graft assembly according to claim 19, wherein the human cadaver donor bone material of the first bone piece comprises cortical bone material.

21. The bone graft assembly according to claim 3, wherein the second bone piece comprises human cadaver donor bone material.

22. The bone graft assembly according to claim 21, wherein the human cadaver donor bone material of the second bone piece comprises cortical bone material.

23. The bone graft assembly according to claim 3, wherein the first bone piece core surface has a first bone piece core surface diameter, wherein the second bone piece core surface has a second bone piece core surface diameter, wherein the first bone piece aperture has a first bone piece aperture diameter, wherein the second bone piece aperture has a second bone piece aperture diameter, and wherein the first bone piece aperture diameter and the second bone piece aperture diameter are both greater than each of the first bone piece core surface diameter and the second bone piece core surface diameter.

24. The bone graft assembly according to claim 3, wherein first and second contour shapes are concentric when the first and second mating features are approximated.

* * * * *